United States Patent
Nagai et al.

(10) Patent No.: US 8,546,758 B2
(45) Date of Patent: Oct. 1, 2013

(54) FOOD QUALITY EXAMINATION DEVICE, FOOD COMPONENT EXAMINATION DEVICE, FOREIGN MATTER COMPONENT EXAMINATION DEVICE, TASTE EXAMINATION DEVICE, AND CHANGED STATE EXAMINATION DEVICE

(75) Inventors: Youichi Nagai, Osaka (JP); Yasuhiro Iguchi, Osaka (JP)

(73) Assignee: Sumitomo Electric Industries, Ltd., Osaka (JP)

( * ) Notice: Subject to any disclaimer, the term of this patent is extended or adjusted under 35 U.S.C. 154(b) by 211 days.

(21) Appl. No.: 13/119,619

(22) PCT Filed: Jul. 24, 2009

(86) PCT No.: PCT/JP2009/063247
§ 371 (c)(1),
(2), (4) Date: Mar. 17, 2011

(87) PCT Pub. No.: WO2010/032553
PCT Pub. Date: Mar. 25, 2010

(65) Prior Publication Data
US 2011/0168895 A1    Jul. 14, 2011

(30) Foreign Application Priority Data
Sep. 22, 2008   (JP) ................................. 2008-243181

(51) Int. Cl.
*G01J 5/20* (2006.01)
*H01L 29/861* (2006.01)
(52) U.S. Cl.
USPC ................ 250/338.4; 250/338.1; 250/339.11; 250/339.1; 257/199
(58) Field of Classification Search
USPC .................... 250/338.4, 338.1, 339.11, 339.1; 257/199
See application file for complete search history.

(56) References Cited

U.S. PATENT DOCUMENTS

| | | | |
|---|---|---|---|
| 2007/0096236 A1 | 5/2007 | Yagyu et al. | |
| 2008/0142714 A1* | 6/2008 | Nagai et al. | 250/332 |
| 2010/0051905 A1 | 3/2010 | Iguchi et al. | |

FOREIGN PATENT DOCUMENTS

| | | |
|---|---|---|
| JP | 63-01079 | 1/1988 |
| JP | 03-38887 | 2/1991 |

(Continued)

OTHER PUBLICATIONS

Yamamoto et al., "Optical properties of GaAs0.5Sb0.5 and In0.53Ga0.47As/GaAs0.5Sb0.5 type II single hetero-structures lattice-matched to InP substrates grown by molecular beam epitaxy", J. of Crystal Growth, Elsevier 201/202, pp. 872-876 (1999).

(Continued)

*Primary Examiner* — David Porta
*Assistant Examiner* — Kenneth J Malkowski
(74) *Attorney, Agent, or Firm* — Fish & Richardson P.C.

(57) ABSTRACT

A food quality examination device using a high-sensitivity light-receiving element. The light-receiving element includes a III-V compound semiconductor stacked structure including an absorption layer having a pn-junction therein, wherein the absorption layer has a multiquantum well structure composed of group III-V compound semiconductors, the pn-junction is formed by selectively diffusing an impurity element into the absorption layer, a diffusion concentration distribution control layer composed of III-V group semiconductor is disposed in contact with the absorption layer on a side of the absorption layer opposite the side adjacent to the group III-V compound semiconductor substrate,
the bandgap energy of the diffusion concentration distribution control layer is smaller than that of the group III-V semiconductor substrate,
the concentration of the impurity element selectively diffused in the diffusion concentration distribution control layer is decreased to be $5\times10^{16}/cm^3$ or less toward the absorption layer.

18 Claims, 15 Drawing Sheets

(56) References Cited

FOREIGN PATENT DOCUMENTS

| JP | 05-160426 | 6/1993 |
|---|---|---|
| JP | 05-160429 | 6/1993 |
| JP | 05-232017 | 9/1993 |
| JP | 08-029335 | 2/1996 |
| JP | 08-029336 | 2/1996 |
| JP | 09-009767 | 1/1997 |
| JP | 09-119894 | 5/1997 |
| JP | 09-219563 | 8/1997 |
| JP | 09-250983 | 9/1997 |
| JP | 09-288056 | 11/1997 |
| JP | 2001-004616 | 1/2001 |
| JP | 2001-144278 | 5/2001 |
| JP | 2002-373999 | 12/2002 |
| JP | 2003-510601 | 3/2003 |
| JP | 2005-233824 | 9/2005 |
| JP | 2006-270060 | 10/2006 |
| JP | 2007-80920 | 3/2007 |
| JP | 2007-093506 | 4/2007 |
| JP | 2007-201432 | 8/2007 |
| JP | 2007-212335 | 8/2007 |
| JP | 2007-225293 | 9/2007 |
| JP | 2007-324572 | 12/2007 |
| JP | 2008-014873 | 1/2008 |
| JP | 2008-153311 | 7/2008 |
| JP | 2008-171885 | 7/2008 |
| JP | 2008-205001 | 9/2008 |
| JP | 2008-270760 | 11/2008 |
| JP | 2008-288293 | 11/2008 |
| WO | 2007/120931 | 10/2007 |

OTHER PUBLICATIONS

Sidhu et al., "A Long-Wavelength Photodiode on InP Using Lattice Matched GaInAs-GaAsSb Type-II Quantum Wells," IEEE Photonics Tech. Letters 17(12):2715-2717 (2005).

Nakayama, M., "Technology trend of infrared detecting elements", Hamamatsu Photonics K.K., 9(3): 61-64 (Mar. 1989).

Kawano, S. (ed.), "Applications of near-infrared spectroscopy to foods" in Handbook of nondestructive measurement for foods, Science Forum, Ch. 3 and 4, pp. 33-40 (2003) (with partial English translation).

* cited by examiner

Incident light

FOOD QUALITY EXAMINATION DEVICE, FOOD COMPONENT EXAMINATION DEVICE, FOREIGN MATTER COMPONENT EXAMINATION DEVICE, TASTE EXAMINATION DEVICE, AND CHANGED STATE EXAMINATION DEVICE

TECHNICAL FIELD

The present invention relates to a food quality examination device, a food component examination device, a foreign matter component examination device, a taste examination device, and a changed state examination device. More specifically, the present invention relates to a food quality examination device using a light receiving element having a high sensitivity up to long wavelengths in the near-infrared region without cooling, a food component examination device, a foreign matter component examination device, a taste examination device, and a changed state examination device using the food quality examination device.

BACKGROUND ART

Biogenic substances of plants and animals, drugs, environment-related substances, and so forth have absorption bands in the near-infrared region. Thus, near-infrared spectroscopy has been receiving attention as a noninvasive analysis. Rapid advances have been made in the development and practical utilization of near-infrared spectroscopy. In particular, the issue of food safety has recently been receiving attention. As described above, absorption spectra of soybeans, rice, starch, and lipid, which belong to plants and animals, are observed in the near-infrared region. Thus, studies on the quality inspection of food using near-infrared spectroscopy have been actively conducted (NPL 1). In near-infrared spectroscopy, output signals contain necessary information and high levels of noise attributed to light receiving elements. The extraction of necessary information from output signals does not entirely depend on the improvement in the performance of sensors (light receiving elements) but is performed by spectroscopic methods, chemometrics, and so forth as important methods.

The foregoing sensors (light receiving elements) are broadly categorized into electron tubes and photodiodes (PDs), which are solid-state components. Among these components, PDs are small and easily integrated in the form of a linear array or a two-dimensional array. Thus, extensive research and development thereof have been conducted (NPL 2). The present invention aims at a food quality examination device including a PD. Nowadays, the following PDs and PD arrays are used.
(1) PDs having sensitivity up to the infrared region and also having sensitivity in the near-infrared region, or an array thereof. Examples of such photodiodes include germanium (Ge)-based PDs, lead sulfide (PbS)-based PDs, HgCdTe-based PDs, linear arrays thereof, and two-dimensional array thereof.
(2) InP-based PDs having sensitivity at wavelengths of 1.7 µm or less in the near-infrared region, InGaAs-based PDs included in InP-based PDs, and arrays thereof. The term "InP-based PDs" indicates PDs having absorption layers composed of III-V group compound semiconductors formed on InP substrates and includes InGaAs-based PDs.

Among these photodiodes, the PDs of item (1) are often cooled to suppress noise. For example, the PDs are often operated at the temperature of liquid nitrogen (77 K) or under cooling with Peltier elements. Thus, large-scale devices are needed, thereby increasing the cost of the devices. Although the PDs can be used at room temperature, the PDs disadvantageously have high dark currents at wavelengths of 2.5 µm or less and poor detection capabilities. The InP-based PDs of item (2) have disadvantages that (I) although InGaAs, which is lattice-matched to InP, has a low dark current, the sensitivity is limited to wavelengths of 1.7 µm or less in the near-infrared region, and (II) extended-InGaAs with sensitivity at extended wavelengths up to 2.6 µm has a high dark current and needs to be cooled. Thus, InP-based PDs cannot use light having a wavelength of 2.0 µm or more, the light being important in the inspection of food, or needs to be cooled when use the light.

light receiving elements that have been used for food quality inspection in the past are described below.
(C1) Methods of food quality inspection using lead sulfide (PbS) are disclosed (PTLs 1 to 4).
(C2) A measurement device using an InGaAs PIN photodiode is used (PTL 5).
(C3) Many literatures do not specifically describe what elements are used as infrared detectors (PTLs 6 to 13).

In the methods of food quality inspection described above, the sensitivities of light receiving elements themselves are not considered. All literatures suggest that what techniques should be used to perform the food quality inspection.

As described above, InGaAs PIN photodiodes have a problem of the need to extend the sensitivities to longer wavelengths in the near-infrared region. To solve the problem, the following measures are reported.
(K1) The In content of an InGaAs absorption layer is increased. A lattice-mismatch to an InP substrate is reduced by interposing a stepped buffer layer therebetween, the In content of the stepped buffer layer being gradually changed (PTL 14).
(K2) N is incorporated into an InGaAs absorption layer to form a GaInNAs absorption layer (PTL 15). A lattice matching to an InP substrate is satisfied by incorporating a large amount of N thereinto.
(K3) The use of a GaAs Sb-InGaAs type-II multiquantum well structure extends the sensitivity to longer wavelengths (NPL 3). The lattice matching to an InP substrate is satisfied.
(K4) A two-dimensional array is formed by forming element separation trenches between light receiving elements (pixels) using wet etching (PTL 16).

Although the measures for improvement are proposed as described above, the extension of the sensitivity to wavelengths of 1.7 µm or more and the suppression of noise and dark current have not been satisfactorily achieved by any of the measures of items (K1) to (K4).

NPL 1: Sumio Kawano, "Syokuhin no Hihakai Keisoku Handbook (Handbook of Nondestructive Measurement for Food)", SCIENCE FORUM, pp. 34-40

NPL 2: Masao Nakayama, "Sekigaisen Kensyutsu Soshi no Gijutu Doukou (Technological Trends in Infrared Radiation Detection Elements)", Sensor Gijutsu (Sensor Technology), March 1989 (Vol. 9, No. 3), pp. 61-64

NPL 3: R. Sidhu, "A Long-Wavelength Photodiode on InP Using Lattice-Matched GaInAs-GaAsSb Type-II Quantum Wells, IEEE Photonics Technology Letters, Vol. 17, No. 12 (2005), pp. 2715-2717

PTL 1: Japanese Unexamined Patent Application Publication No. 2005-233824

PTL 2: Japanese Unexamined Patent Application Publication (Translation of PCT Application) No. 2003-510601

PTL 3: Japanese Unexamined Patent Application Publication No. 8-29336

PTL 4: Japanese Unexamined Patent Application Publication No. 8-29335
PTL 5: Japanese Unexamined Patent Application Publication No. 2007-93506
PTL 6: Japanese Unexamined Patent Application Publication No. 9-9767
PTL 7: Japanese Unexamined Patent Application Publication No. 5-232017
PTL 8: Japanese Unexamined Patent Application Publication No. 2001-4616
PTL 9: Japanese Unexamined Patent Application Publication No. 2007-212335
PTL 10: Japanese Unexamined Patent Application Publication No. 2007-225293
PTL 11: Japanese Unexamined Patent Application Publication No. 9-119894
PTL 12: Japanese Unexamined Patent Application Publication No. 9-250983
PTL 13: Japanese Unexamined Patent Application Publication No. 9-288056
PTL 14: Japanese Unexamined Patent Application Publication No. 2002-373999
PTL 15: Japanese Unexamined Patent Application Publication No. 9-219563
PTL 16: Japanese Unexamined Patent Application Publication No. 2001-144278

SUMMARY OF INVENTION

Technical Problem

As described in items (K1) to (K4), there are some candidates for a light receiving element or a light receiving element array which need not be cooled with liquid nitrogen or a Peltier element and which has sensitivity at long wavelengths in the near-infrared region. However, there are many difficult problems to be overcome to realize practical use, for example, low crystal quality, a high dark current, and difficulty in production. Thus, such a light receiving element and a light receiving element array are still under development. Hence, a measurement using a photodiode without a cooling mechanism leads to a high level of noise. However, it is very significant that the performance of a light receiving element is improved to produce an appropriate food quality examination device suitable for a test object in accordance with the feature of the improvement in the performance. That is, if high-sensitivity near-infrared spectroscopy can be performed using a photodiode in which a dark current is suppressed without using a cooling mechanism, useful information about food can be easily obtained. Thus, development in many fields related to food can be promoted.

It is an object of the present invention to provide a food quality examination device configured to inspect the quality of food with high sensitivity using an InP-based photodiode in which a dark current is decreased without a cooling mechanism and the sensitivity is extended to a wavelength of 1.8 μm or more. It is another object of the present invention to provide a food component examination device, a foreign matter component examination device, a taste examination device, and a changed state examination device including the photodiode.

Solution to Problem

A food quality examination device according to the present invention includes a light receiving element composed of III-V group semiconductor or an array of the light receiving elements, the light receiving element being configured to receive near-infrared light, and the food quality examination device being configured to detect the quality of food. In this device, the light receiving element includes an absorption layer with a multiquantum well structure formed on an InP substrate. The absorption layer has a bandgap wavelength of 1.8 μm to 3 μm. A diffusion concentration distribution control layer composed of III-V group semiconductor is disposed in contact with the absorption layer on a side of the absorption layer opposite the side adjacent to the InP substrate (i.e., the diffusion concentration distribution control layer is located in such a manner that the absorption layer is provided between the diffusion concentration distribution control layer and the InP substrate). The bandgap of the diffusion concentration distribution control layer is lower than that of the InP. In the light receiving element, a pn junction is formed by selectively diffusing an impurity element through the diffusion concentration distribution control layer to reach the absorption layer. The concentration of the impurity element selectively diffused in the diffusion concentration distribution control layer is decreased $5 \times 10^{16}$/cm$^3$ or less toward the absorption layer. The light receiving element receives light coming through or reflected from the food, the light having at least one wavelength of 3 μm or less, thereby performing the inspection.

In the foregoing structure, the multiquantum well structure has a bandgap energy corresponding to the near-infrared region and the diffusion concentration distribution control layer has a reduced impurity concentration of $5 \times 10^{16}$ cm$^{-3}$ or less. Thus, the multiquantum well structure is not broken. That is, the multiquantum well structure is formed without reducing the crystal quality. To form a pn junction of the light receiving element, the impurity is selectively diffused. That is, the impurity is introduced into a portion inner than the peripheral portion of each light receiving element in such a manner that the diffusion is two-dimensionally limited and that light receiving elements are separated. Thus, each light receiving element is easily formed with high accuracy. There is no need to form an element separation trench. It is thus possible to form the light receiving element having a low dark current. So, it is possible to receive light at a wavelength of 3 μm or less with high sensitivity without using cooling. Absorption bands of components (molecules) contained in food are often present in a wavelength range of 1.2 μm to 3 μm. Thus, the food inspection can be performed with satisfactory sensitivity.

The bandgap of the diffusion concentration distribution control layer is lower than that of the InP. Thus, even if a portion of the diffusion concentration distribution control layer adjacent to the absorption layer has a low impurity concentration, the electrical resistance can be reduced, thereby preventing a reduction in response speed. More specifically, the reason that the bandgap of the diffusion concentration distribution control layer is lower than that of the InP is as follows.

(1) When the absorption layer used for the near-infrared region is composed of a III-V group compound semiconductor, a window layer having a bandgap energy larger than that of the absorption layer is sometimes used. In this case, a material the same as the semiconductor substrate is often used in view of lattice matching and so forth, provided that the bandgap energy of the diffusion concentration distribution control layer is lower than that of the window layer and larger than that of the absorption layer. This is because if the bandgap energy of the diffusion concentration distribution control layer is lower than that of the absorption layer, the diffusion concentration distribution control layer absorbs the light to reduce the sensitivity of the absorption layer when a structure in which light is incident on the surface of an epitaxial layer is used.

(2) The use of a material having a lower bandgap energy than that of a material that is usually used for the window layer reduces the degree of an increase in electrical resistance or the degree of a reduction in electrical conductivity even at a lower impurity concentration, thereby suppressing a reduction in response speed under an applied voltage, as described above.

Here, the term "inspection" may indicate that a calibration curve of a predetermined component (the relationship between the concentration of the predetermined component and the intensity or absorption of light at the wavelength) is produced in advance to determine the concentration or content of the predetermined component. Alternatively, the term "inspection" may be a method that does not use such a calibration curve. Note that the pn junction should be widely construed as described below. A region adjacent to a side of the absorption layer opposite the side into which the impurity element is introduced by selective diffusion is an impurity region (referred to as an "i region") having a low impurity concentration and may be regarded as an intrinsic semiconductor. The pn junction also includes a junction formed between the i region and the region into which the impurity is introduced by diffusion. That is, the foregoing pn junction may be a pi junction or an ni junction. Furthermore, the pn junction includes the pi junction or the ni junction in which the p concentration or the n concentration is very low.

The of concentration of the impurity element in the region located adjacent to a surface of the diffusion concentration distribution control layer opposite the surface in contact with the absorption layer being about $1\times10^{18}/cm^3$ or more.

This ensures satisfactory crystal quality of the multiquantum well structure while suppressing the interface resistance of an electrode located on the top surface or while enabling the formation of an ohmic contact. A problem of an increase in electrical resistance or a reduction in electrical conductivity in a portion of the diffusion concentration distribution control layer due to a low impurity concentration can be reduced by reducing the bandgap energy of the diffusion concentration distribution control layer to a level lower than that corresponding to the bandgap energy of InP, as described above.

A pile-up of selectively diffused impurity element is present at the boundary between the diffusion concentration distribution control layer and the absorption layer.

The distribution of high impurity element concentration due to the pileup decreases precipitously with a skirt shape in the absorption layer. For this reason, in the case that the concentration of the opposite conductivity-type carrier is relatively high in spite of non-doping, the pn-junction may be surely formed in the absorption layer, and positioned near the upper surface of the absorption layer. As a result, the depletion layer, and the sensitivity may be increased. In addition, as the pile-up does not quite enter within the diffusion concentration distribution layer, the influence to the absorption layer is small. For this reason, the limitation of the concentration of the impurity element ($5\times10^{16}/cm^3$ or less) is not obviously applied to the concentration of the piled-up impurity in accordance with the drift of this invention. But even if it applied, the peak concentration of the pile-up is usually $5\times10^{16}/cm^3$ or less, and it is satisfied with the above concentration limitation ($5\times10^{16}/cm^3$ or less.)

The absorption layer may have a type-II quantum well structure. This enables an electron to cause a transition from a high valence band layer to a low conduction band layer when an electromagnetic wave is absorbed, thereby facilitating the acquisition of the sensitivity to light having a longer wavelength.

The absorption layer may have a multiquantum well structure of (InGaAs/GaAsSb) or a multiquantum well structure of (GaInNAs(P, Sb)/GaAsSb). Thus, the light receiving element having excellent crystal quality and having only a low dark current can be easily produced by accumulated techniques and materials.

The InP substrate may be an off-angle substrate that is tilted at an angle of 5° to 20° from the (100) in the [111] direction or in the [11-1] direction. This results in a laminate that includes the absorption layer having the multiquantum well structure with a low defect density and excellent crystal quality. As a result, it is possible to obtain the absorption layer having a suppressed dark current and only a small number of dark dots.

The impurity element may be zinc (Zn), and the diffusion concentration distribution control layer may be composed of InGaAs. It is thus possible to form the diffusion concentration distribution control layer composed of a material in which the dependence of the electrical resistance on impurity concentration is small and the electrical resistance is not very high even at a low impurity concentration. The suppression of an increase in electrical resistance prevents a reduction in response speed. Furthermore, the selective diffusion of zinc serving as an impurity is tried and true. It is possible to form a diffusion region with high accuracy. This makes it possible to prevent an increase in electrical resistance in a lower portion of the diffusion concentration distribution control layer while achieving a high impurity concentration in an upper portion of the diffusion concentration distribution control layer into which the impurity is introduced by diffusion and achieving a low impurity concentration in the lower portion of the diffusion concentration distribution control layer adjacent to the absorption layer. It is thus possible to prevent the formation of a region with a high impurity concentration in the absorption layer having the quantum well structure, thereby producing the light receiving element having satisfactory crystal quality without reducing responsiveness. Note that InGaAs has a bandgap energy of 0.75 eV.

An InP window layer may be disposed on the diffusion concentration distribution control layer. The formation of the window layer composed of InP does not reduce the crystal quality of the semiconductor laminated structure therein and is effective in suppressing a dark current while, for example, the absorption of near-infrared light is prevented on the incident light side of the absorption layer when a structure in which light is incident on the epitaxial layer is used. Furthermore, a technique for forming a passivation film on the crystal surface of InP is accumulated and established, as compared with the case of forming a passivation film on another crystal surface, for example, a technique for forming a passivation film on the surface of InGaAs. It is thus possible to easily suppress current leakage on the surface.

The degree of lattice matching ($|\Delta a/a|$, where a represents a lattice constant, and $\Delta a$ represents a difference in lattice constant among the InP substrate, sublayers constituting the quantum well structure of the absorption layer, the diffusion concentration distribution control layer, and the InP window layer) may be 0.002 or less. This results in the absorption layer having excellent crystal quality using a commonly available InP substrate. Thus, for the light receiving element for near-infrared light having a wavelength of 1.8 μm or more or the array of the light receiving elements, a dark current can be markedly suppressed.

Here, in the array of the light receiving elements, the common semiconductor laminated structure is used for the plural light receiving elements. The impurity element is selectively diffused into the absorption layer for each light receiving element to form impurity diffusion regions that are one-dimensionally or two-dimensionally arranged. This structure eliminates the need to form an element separation trench because each of the light receiving elements has a corresponding one of the impurity diffusion regions, thereby easily forming the array of the light receiving elements with high accuracy and a low dark current.

The food quality examination device may further include a spectrometer unit arranged at the front or back of the food that is a test object, the spectrometer unit being configured to separate light spectroscopically, and a controller configured to perform an arithmetic operation on the basis of the result of the reception of light by the light receiving elements or the array of the light receiving elements to calculate an evaluation value of the quality of the food, in which the plural light receiving elements or the array of the light receiving elements is located in response to the wavelength of the separated light. In this case, for example, multiwavelength light simultaneous reception can be rapidly performed with good accuracy. The spectrometer unit preferably includes a diffraction grating. The controller includes, as a matter of course, a storage unit, an input unit from the outside, and so forth. For example, a calibration curve for the target wavelength may be input and stored.

The food that is a test object may be irradiated with light emitted from a supercontinuum light source (SC light source) or a light-emitting diode (LED), and light coming through or reflected from the food that is the test object may be received. Usually, a halogen lamp is used as a light source. However, the irradiation with the halogen lamp can degrade the freshness of the food because of heat generation from the halogen lamp. In contrast, the SC light source and the LED do not generate heat and thus are suitable for light sources that are used to measure the quality of food. In the cases of using the SC light source, the LED, and the typical halogen lamp, the food inspection device according to the present invention usually includes the controller configured to perform an arithmetic operation on the basis of the result of the reception of light by the light receiving elements or the array of the light receiving elements to calculate an evaluation value of the quality of the food.

The food quality examination device may further include an imaging device including a two-dimensional array of the light receiving elements. The imaging device may form a distribution image of a substance contained in the food that is a test object. It is thus possible to form the understandable distribution image of a predetermined component in the test object.

In a structure in which the InP substrate is located on an incident light side, the InP substrate may be removed. In the case where mounting is performed in such a manner that the InP substrate is located on an incident light side, the removal of the InP substrate enables the absorption layer to receive and detect light having a wavelength of 1000 nm or less.

A food component examination device according to the present invention includes one of the food quality examination devices described above, in which the food component examination device detects a component contained in the food. This makes it possible to detect, for example, the sugar content of fruit, fat in beef and eels, and water and protein in cereals. Furthermore, for example, the food component examination device can also be used to identify special local food in an area (identification of differences with the same food in other areas). Note that the term "identification" used here may include not only the identification of food in a strict sense but also simple detection of the characteristics.

The concentration distribution or the like of the component contained in the food may be detected in a specific range to identify the production area, the place of origin, the brand, and so forth of the food. Thus, an inferior product can be nondestructively identified, thereby contributing to the protection of, for example, the right of trademark. Furthermore, when a food product is shipped, for example, a food product with a specific component that is outside a predetermined concentration distribution is discarded, thereby maintaining the quality of a special product in a specific production area or maintaining the quality of a special product in which the registered trademark is protected.

A foreign matter component examination device according to the present invention includes one of the food quality examination devices described above, in which the foreign matter component examination device detects foreign matter. This makes it possible to easily and rapidly detect, for example, a hazardous substance contained in food and contribute to food safety.

A taste examination device according to the present invention includes one of the food quality examination devices described above, in which the taste examination device inspects the food for taste. This makes it possible to inspect the quality, such as taste, which is complicated and difficult to evaluate. For this purpose, it is necessary to measure the absorption of light at many wavelengths in a longer wavelength range of the near-infrared region.

A changed state examination device according to the present invention includes one of the food quality examination devices described above, in which the changed state examination device inspects the food for the current state of the changeable quality, such as a processing state and a freshness state. This ensures food safety.

Advantageous Effects of Invention

According to the present invention, it is possible to provide a food quality examination device configured to inspect the quality of food with high sensitivity using an InP-based photodiode in which a dark current is decreased without a cooling mechanism and the sensitivity is extended to a wavelength of 1.8 μm or more. Furthermore, it is possible to provide a food component examination device, a foreign matter component examination device, a taste examination device, and a changed state examination device including the photodiode.

BRIEF DESCRIPTION OF DRAWINGS

FIG. 1 is a cross-sectional view of a light receiving element according to a first embodiment of the present invention.

FIG. 2 illustrates distribution of Zn concentration in the light receiving element illustrated in FIG. 1.

FIG. 3 is a cross-sectional view of a light receiving element array according to the first embodiment of the present invention.

FIG. 4 is a cross-sectional view of a light receiving element according to a first reference embodiment different from the present invention.

FIG. 5 illustrates the distribution of Zn concentration in the light receiving element illustrated in FIG. 4.

FIG. 6 is a cross-sectional view of a light receiving element according to a second reference embodiment different from the present invention.

FIG. 7 illustrates the distribution of Zn concentration in the light receiving element illustrated in FIG. 6.

FIG. 8 illustrates the outline of an imaging device according to a second embodiment of the present invention.

FIG. 9 illustrates a light receiving element array of the imaging device illustrated in FIG. 8.

FIG. 10 illustrates a single light receiving element of the light receiving element array illustrated in FIG. 9.

FIG. 11 is a cross-sectional view of an epi-side-up mounted light receiving element.

FIG. 12 is a cross-sectional view of an epi-side-down (flip-chip) mounted light receiving element.

FIG. 13 illustrates a food component examination device (1) according to a third embodiment of the present invention.

FIG. 14 illustrates a spectrometer unit and a light receiving unit of the food component examination device illustrated in FIG. 13.

FIG. 15 illustrates the spectrometer unit and a controller.

FIG. 16 illustrates a food component examination device (2) according to a fourth embodiment of the present invention.

FIG. 17 illustrates the arrangement of a test object in the food component examination device illustrated in FIG. 16.

FIG. 18 illustrates a change in the distribution of a specific component in a foodstuff with time.

FIG. 19 illustrates a state in which a beef carcass is inspected with a food component examination device (3) according to a fifth embodiment of the present invention.

FIG. 20 illustrates the food component examination device illustrated in FIG. 19.

FIG. 21 is a foreign matter component examination device according to a seventh embodiment of the present invention.

FIG. 22 illustrates a taste examination device according to a ninth embodiment of the present invention.

FIG. 23 illustrates near-infrared absorption spectra of three brands of rice.

FIG. 25 is a partially cross-sectional view of a light receiving element array used in an example.

FIG. 26 illustrates the relationship between the element spacing and the dark current measured in an example.

FIG. 27 illustrates the distribution of Zn concentration in the depth direction in an example.

DESCRIPTION OF EMBODIMENTS (First Embodiment—Structure of Semiconductor Light Receiving Element Array—)

Figure 1:
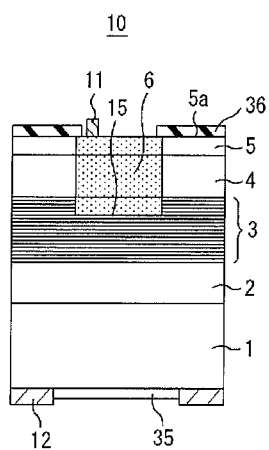
[FIG. 1]

FIG. 1 is a cross-sectional view of a light receiving element 10 according to an embodiment of the present invention. Referring to FIG. 1, the light receiving element 10 includes a following III-V group semiconductor laminated structure (epitaxial wafer) on an InP substrate 1:

(InP substrate 1/InP buffer layer 2/absorption layer 3 with a multiquantum well structure composed of InGaAs or GaInNAs and GaAs Sb/InGaAs diffusion concentration distribution control layer 4/InP window layer 5).

A p-type region 6 extending from the InP window layer 5 to the absorption layer 3 having the multiquantum well structure is formed by selectively diffusing Zn, which serves as a p-type impurity, through an opening of a selective diffusion mask pattern 36 made of a SiN film. The p-type impurity is introduced by selective diffusion into a portion inner than the peripheral portion of the light receiving element 10 using the selective diffusion mask pattern 36 made of the SiN film in such a manner that the diffusion is two-dimensionally limited.

A p-side electrode 11 composed of AuZn is provided on the p-type region 6, and an n-side electrode 12 is provided on the back surface of the InP substrate 1, each of the p-side electrode 11 and the n-side electrode 12 being provided so as to form an ohmic contact. In this case, the InP substrate 1 is doped with an n-type impurity, thereby ensuring a predetermined level of conductivity. An antireflection film 35 composed of SiON is provided on the back surface of the InP substrate 1 in such a manner that the light receiving element 10 can also be used when light is incident from the back surface of the InP substrate 1.

In the absorption layer 3 with the multiquantum well structure, a pn junction 15 is formed at a position corresponding to a boundary front of the p-type region 6. The application of a reverse bias voltage between the p-side electrode 11 and the n-side electrode 12 results in the formation of a wider depletion layer in a portion having a low n-type impurity concentration (n-type impurity background). The background in the absorption layer 3 having the multiquantum well structure is about $5 \times 10^{15}/cm^3$ or less in terms of the n-type impurity concentration (carrier concentration). A position of the pn-junction 15 is determined by the intersecting point of the background (n-type carrier concentration) of the absorption layer 3 having the multiquantum well structure and the concentration profile of Zn serving as a p-type impurity. That is, the pn-junction 15 is located at a position illustrated in FIG. 2.

Figure 2:
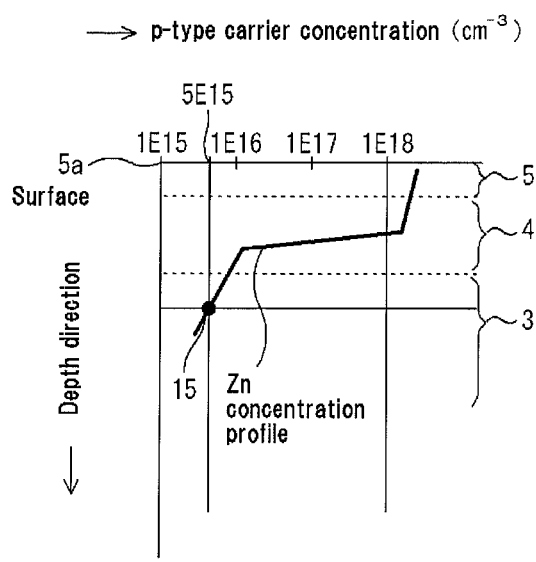
[FIG. 2]

In the diffusion concentration distribution control layer 4, the concentration of the p-type impurity that has been selectively diffused from a surface 5$a$ of the InP window layer 5 is steeply reduced from a high-concentration region adjacent to the InP window layer 5 to the absorption layer 3 side. It is thus possible to easily achieve a Zn concentration, which is an impurity concentration, of $5 \times 10^{16}/cm^3$ or less in the absorption layer 3. In FIG. 2, about $1 \times 10^{16}/cm^3$ or less, which is lower than the above value, of the Zn concentration is achieved in the absorption layer 3.

The light receiving element 10 according to the present invention aims to have sensitivity in the near-infrared region and longer wavelengths thereof. Thus, the window layer 5 is preferably composed of a material having a higher bandgap energy than the absorption layer 3. So, InP, which has a higher bandgap energy than the absorption layer and exhibits good lattice matching, is typically used for the window layer 5. Alternatively, InAlAs, which has a bandgap energy substantially equal to that of InP, may be used.

(Features of Light Receiving Element Array According to This Embodiment)

The light receiving element array according to this embodiment is characterized by including the following factors.

1. In the case where an impurity is introduced by selective diffusion into a multiquantum well structure at a high concentration, the structure will be broken. Thus, the impurity needs to be introduced by selective diffusion in such a manner that the impurity concentration is suppressed to be a low level. Typically, the concentration of the p-type impurity introduced by diffusion needs to be $5 \times 10^{16}/cm^3$ or less.

2. To stably achieve the foregoing low p-type-impurity concentration with good reproducibility in actual production, the InGaAs diffusion concentration distribution control layer 4 is provided on the absorption layer 3. In the case where a portion of a diffusion concentration distribution control layer 4 adjacent to the absorption layer 3 has the foregoing low impurity concentration, the portion with the low impurity concentration has a reduced electrical conductivity or an increased electrical resistance. A reduction in the electrical conductivity of the portion of the diffusion concentration distribution control layer 4 having the low impurity concentration reduces responsibility, thereby failing to provide, for example, a satisfactory moving image. However, in the case where the InGaAs diffusion concentration distribution control layer 4 is composed of a material having a lower bandgap energy than a bandgap energy comparable to that of InP, specifically, a III-V group semiconductor material having a bandgap energy less than 1.34 eV, the electrical conductivity is not significantly reduced even at a low impurity concentration. An example of the III-V group semiconductor material that satisfies the requirement of the diffusion concentration distribution control layer is InGaAs.

The use of the InGaAs diffusion concentration distribution control layer 4 composed of a material having a low bandgap energy results in the suppression of an increase in electrical resistance even at a low impurity concentration. It is believed that a response speed to the application of a reverse bias voltage and so forth depends on a CR time constant determined by a capacitance and the electrical resistance. Thus, the suppression of the increase in electrical resistance R as described above results in an increase in response speed.

3. In this embodiment, the multiquantum well structure has a type-II structure. With respect to a type-I multiquantum well structure, for a light receiving element having sensitivity in the near-infrared region and including a semiconductor layer having a low bandgap energy provided between semiconductor layers each having high bandgap energy, the upper limit of the wavelength (cut-off wavelength) of the sensitivity is determined by the bandgap of the semiconductor layer having a low bandgap energy. That is, the transition of electrons or holes caused by light is performed in the semiconductor layer having a low bandgap energy (direct transition). In this case, a material that can extend the cut-off wavelength to a longer wavelength is very limited among III-V group compound semiconductors. In contrast, with respect to the type-II multiquantum well structure, in the case where two different semiconductor layers having a common Fermi energy are alternately laminated, a difference in energy between the conduction band of a first semiconductor and the valence band of a second semiconductor determines the upper limit of the wavelength (cut-off wavelength) of the sensitivity. That is, the transition of electrons or holes caused by light is performed between the valence band of the second semiconductor and the conduction band of the first semiconductor (indirect transition). Thus, a higher energy of the valence band of the second semiconductor than the energy of the valence band of the first semiconductor and a lower energy of the conduction band of the first semiconductor than the energy of the conduction band of the second semiconductor are more likely to achieve the sensitivity extending to a longer wavelength than the case of the direct transition in a single semiconductor.

4. As described above, the p-type impurity is introduced by selective diffusion into the portion inner than the peripheral portion of the light receiving element 10 using the selective diffusion mask pattern in such a manner that the diffusion is two-dimensionally limited. Thus, the pn junction 15 is not exposed at an end face of the light receiving element 10, thereby suppressing the leakage of photocurrent.

Figure 3:
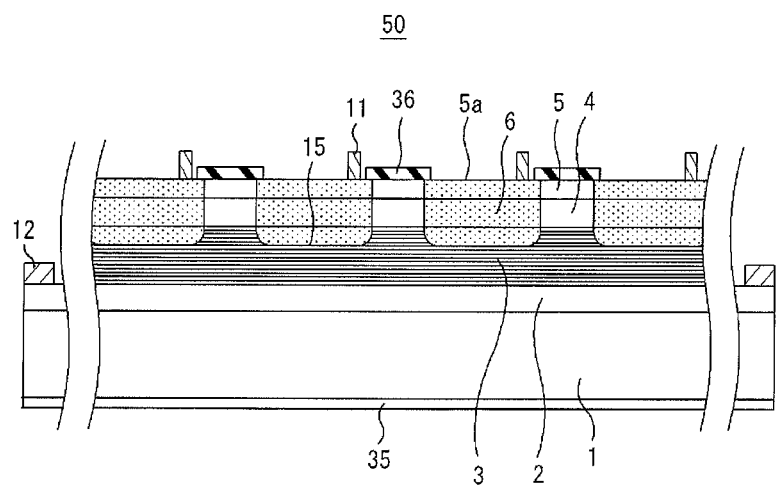
[FIG. 3]

FIG. 3 is a cross-sectional view of a light receiving element array 50 in which a plurality of the light receiving elements 10 are arranged on an epitaxial wafer including the common InP substrate 1. The light receiving element array 50 is characterized by the arrangement of the plural light receiving elements without an element separation trench. As described in item 4, each of the p-type regions 6 is limited to the inner portion of a corresponding one of the light receiving elements. Adjacent light receiving elements are reliably separated from each other. For example, the absorption layer 3 has a multiquantum well structure, the diffusion concentration distribution control layer 4 is disposed on the absorption layer 3, and the absorption layer 3 has a p-type impurity concentration of $5 \times 10^{16}/cm^3$ or less, which are the same as in the light receiving element 10 illustrated in FIG. 1.

A method for producing the light receiving element 10 illustrated in FIG. 1 will be described below. The InP buffer layer 2 or an InGaAs buffer layer 2 having a thickness of 2 μm is formed on the InP substrate 1. The absorption layer 3 having a multiquantum well structure of (InGaAs/GaAsSb) or (GaInNAs/GaAsSb) is formed. An InGaAs layer (or a GaInNAs layer) included in each quantum well structure unit has a thickness of 5 nm. The number of pairs (the number of repetitions of the quantum well units) is 300. Then an InGaAs layer having a thickness of 1 μm is epitaxially grown on the absorption layer 3 and functions as the diffusion concentration distribution control layer 4 for the introduction of Zn by diffusion. Finally, the InP window layer 5 having a thickness of 1 μm is epitaxially grown. Preferably, both the absorption layer 3 and the diffusion concentration distribution control layer 4 are epitaxially grown by molecular beam epitaxy (MBE). The InP window layer 5 may also be epitaxially grown by MBE. Alternatively, after the growth of the diffusion concentration distribution control layer 4, the substrate is taken out from an MBE apparatus, and then the InP window layer 5 may be epitaxially grown by metal organic vapor phase epitaxy (MOVPE).

The InP buffer layer 2 or the InGaAs buffer layer 2 may be undoped or may be doped with an n-type dopant, such as Si, in a concentration of about $1 \times 10^{17}/cm^3$. The absorption layer 3 having a multiquantum well structure of GaInNAs/GaAsSb, the InGaAs diffusion concentration distribution control layer 4, and the InP window layer 5 are preferably undoped but may be doped with a trace amount of (e.g., about $2 \times 10^{15}/cm^3$) of an n-type dopant, such as Si. Furthermore, an n-side electrode-forming layer configured to form an n-side electrode, the n-side electrode-forming layer being doped with an n-type dopant in a high concentration of about 1E18 $cm^{-3}$, may be formed between the InP substrate 1 and the buffer layer 2. The InP substrate 1 may be an Fe-doped semi-insulating InP substrate. In this case, the n-side electrode-forming layer doped with an n-type dopant in a concentration of about $1 \times 10^{18}/cm^3$ is formed between the semi-insulating InP substrate 1 and the buffer layer 2.

An optical device is produced using the laminated structure (epitaxial wafer) including the InP substrate 1. The selective diffusion mask pattern 36 composed of SiN is formed on the surface 5a of the InP window layer 5. Zn is selectively diffused through openings of the selective diffusion mask pattern 36, so that the p-type regions 6 are formed so as to extend to the absorption layer 3 having a multiquantum well structure of InGaAs/GaAsSb (or GaInNAs/GaAsSb). Front end portions of the p-type regions 6 form the pn junctions 15. In this case, high-concentration regions each having a Zn concentration of about $1 \times 10^{18}/cm^3$ or more are limited to the inner portions of the InGaAs diffusion concentration distribution control layers 4. That is, the distribution of the high-concentration impurity is continuous from the surface 5a of each InP window layer 5 to the inner portion of a corresponding one of the InGaAs diffusion concentration distribution control layers 4 in the thickness direction. The concentration of the impurity is reduced to $5 \times 10^{16}/cm^3$ or less at a deeper position of each InGaAs diffusion concentration distribution control layer 4. The Zn-concentration distribution in the vicinity of each pn junction 15 is a distribution that exhibits a graded junction.

In a linear or two-dimensional array of the light receiving elements 10, i.e., in the light receiving element array 50 illustrated in FIG. 3, adjacent light receiving elements are separated by the selective diffusion of Zn (diffusion that is two-dimensionally limited in such a manner that a diffused portion is located in a portion inner than the peripheral portion of each light receiving element) without performing mesa-etching for element isolation. That is, each Zn selective diffusion region 6 forms a main portion of one light receiving element to form a single pixel. Regions where Zn is not diffused separate adjacent pixels. Thus, the light receiving elements do not suffer from, for example, a crystal damage due to mesa-etching, thereby suppressing a dark current.

Patent Document 2 describes the following concern: In the case where a pn junction is formed by selective diffusion of an impurity, the impurity diffuses not only in the depth direction but also in the transverse direction (the direction orthogonal to the depth direction). It is thus impossible to reduce the distance between elements to a certain distance or less. However, results of the actual selective diffusion of Zn demonstrated that for a structure in which the InP window layer 5 is disposed on the top surface and the InGaAs diffusion concentration distribution control layer 4 is disposed under the window layer 5, the extent of diffusion in the transverse direction is substantially equal to or lower than the extent of diffusion in the depth direction. That is, in the selective diffusion of Zn, Zn diffuses in the transverse direction, so that the diameter of a diffusion region is larger than the opening diameter of the mask pattern. However, the extent of the diffusion in the transverse direction is low. The diffusion region is only slightly expanded from the opening of the mask pattern as schematically illustrated in, for example, FIGS. 1 and 3.

Figure 4:
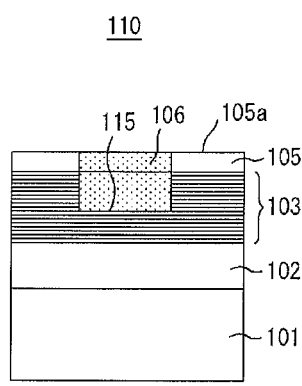
[FIG. 4]

FIG. 4 is a cross-sectional view of a light receiving element 110 according to a first reference embodiment different from the present invention. The light receiving element 110 according to the first reference embodiment has the following laminated structure:
(InP substrate 101/InP or InGaAs buffer layer 102/absorption layer 103 with a multiquantum well structure composed of (GaInNAs/GaAsSb)/InP window layer 105).

This laminated structure differs from the laminated structure according to an embodiment of the present invention in that the diffusion concentration distribution control layer is not provided. Specifically, the absorption layer 103 having a multiquantum well structure is disposed directly below the InP window layer 105.

Figure 5:
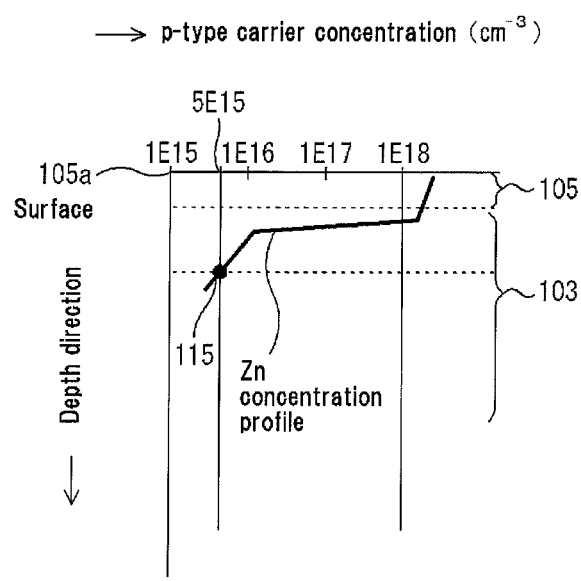
[FIG. 5]

In the case where the diffusion concentration distribution control layer is not provided, as illustrated in FIG. 5, for example, with respect to the distribution of Zn concentration, a high Zn concentration is observed up to the absorption layer 103 having a multiquantum well structure. That is, a region having a high impurity concentration of $1 \times 10^{18}/cm^3$, which exceeds $5 \times 10^{16}/cm^3$, is formed in the multiquantum well structure. The introduction of an impurity into a multiquantum well structure at a high concentration causes the breakage of the structure, thereby significantly increasing a dark current. To prevent the formation of such a high-concentration impurity region in the multiquantum well structure, the diffusion concentration distribution control layer is provided, and the selective diffusion is performed.

However, there is a room for realizing the following ideas regarding the selective diffusion of Zn:
(1) the time required for introduction by diffusion is limited to a short time in such a manner that a high-concentration region does not extend to the multiquantum well structure of the absorption layer 103; and
(2) an increase in the thickness of the InP window layer 105 allows the InP window layer 105 to serve as a diffusion concentration distribution control layer.

Figure 6:
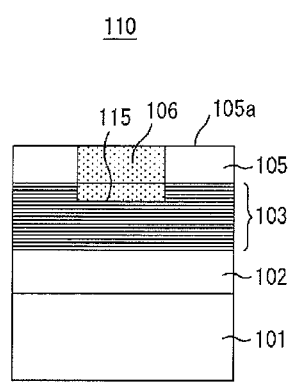
[FIG. 6]
Figure 7:
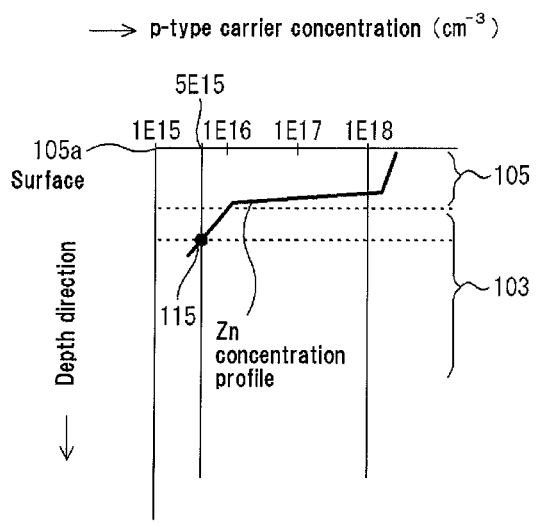
[FIG. 7]

FIG. 6 is a cross-sectional view of the light receiving element 110 according to a second reference embodiment for examining the cases described in items (1) and (2). The light receiving element 110 according to the second reference embodiment has a laminated structure substantially equal to that of the light receiving element according to the first reference embodiment. However, the thickness of the InP window layer 105 according to the second reference embodiment is larger than that of the InP window layer 105 according to the first reference embodiment. The light receiving element 110 corresponds to the case of item (2). In addition, the light receiving element 110 can be used for examining the case of item (1). FIG. 7 illustrates the distribution of Zn concentration obtained when the selective diffusion is performed in the laminated structure illustrated in FIG. 6 so as not to form a high-concentration region of Zn in the multiquantum well structure 103. In the case of the distribution of Zn concentration illustrated in FIG. 7, the Zn concentration is steeply reduced from a high concentration to a low concentration in the InP window layer 105. A low-concentration impurity region having an impurity concentration of about $1 \times 10^{16}/cm^3$ is formed in the InP window layer 105 at a portion of the InP window layer 105 adjacent to the absorption layer 103.

The formation of the low-concentration impurity region having an impurity concentration of about $1 \times 10^{16}/cm^3$ in the InP window layer 105 leads to an increase in the electrical resistance in the region and a reduction in response speed, as repeatedly described above. Thus, a material having a bandgap energy that is large enough to form the window layer, more specifically, the window layer 105 composed of InP, which is a typical material therefor, cannot serve as the diffusion concentration distribution control layer. This applies to both cases of items (1) and (2). Accordingly, a material having a bandgap energy lower than or comparable to that of InP, specifically, a material having a bandgap energy of less than 1.34 eV, is preferably used for the diffusion concentration distribution control layer. That is, it is necessary to use a material, such as InGaAs, having a relatively small reduction in electrical conductivity and a relatively small increase in electrical resistance even in a low-concentration impurity region.

(Second Embodiment—Structure of Imaging Device (Composition Distribution Imaging Device) in Food Composition or Foreign Matter Component Examination Device—)

Figure 8:
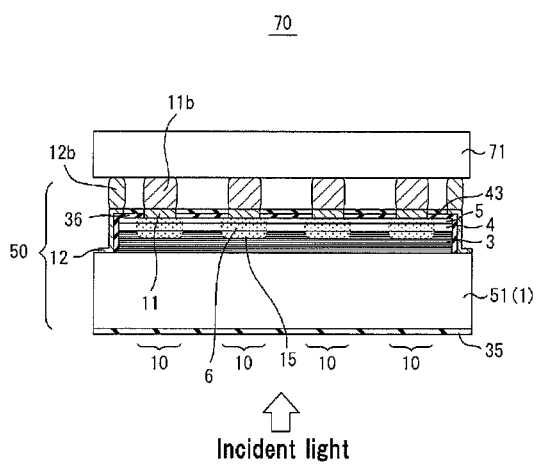
[FIG. 8]
Figure 9:
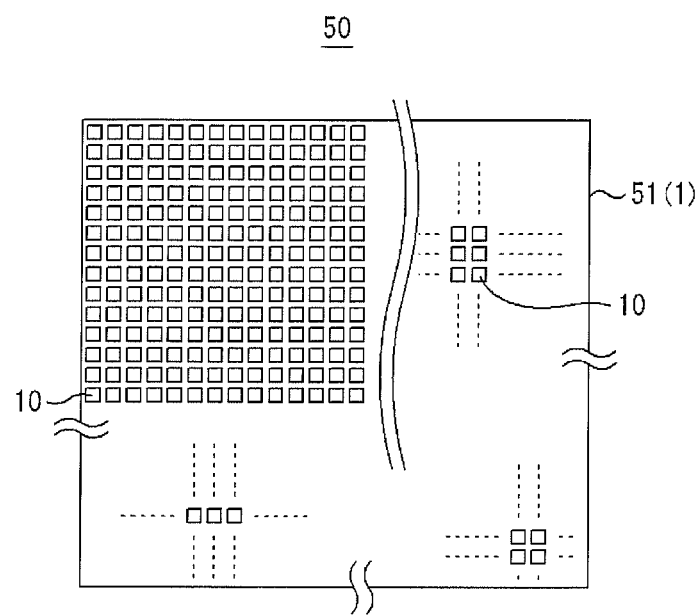
[FIG. 9]
Figure 10:
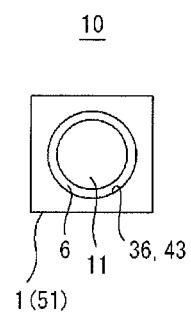
[FIG. 10]

FIG. 8 illustrates the outline of an imaging device 70 (light receiving element array) included in a food composition or foreign matter component examination device according to a second embodiment of the present invention. Optical components, such as a lens, are omitted. FIG. 9 is an explanatory view of the light receiving element array 50 of the foregoing imaging device. FIG. 10 illustrates one of the light receiving elements 10 in the light receiving element array 50 illustrated in FIG. 9. Referring to FIG. 8, in the case of the imaging device 70, the light receiving elements 10 provided on a common InP substrate 51 are epi-side-down mounted in such a manner that the epitaxial layer sides thereof are adjacent to a multiplexer 71 serving as a mounting substrate. The p-side electrode 11 electrically connected to the p-type region 6 of the epitaxial layer of each of the light receiving elements 10 and the n-side electrode 12 provided on the common n-type InP substrate 51 (1) are connected to the multiplexer 71 and send electrical signals to the multiplexer 71. The multiplexer 71 receives the electrical signals from the light receiving elements 10 and performs a process for forming a whole image of an object. The n-side electrode 12 and the p-side electrodes 11 are electrically connected to the multiplexer 71 through solder bumps 12b and 11b, respectively. Incident light is incident on the antireflection (AR) film 35 provided on the back surface of the InP substrate 51 and is received at the pn junctions 15 serving as interfaces between the p-type regions 6 and the absorption layer 3. The p-type regions 6 are formed through the openings of the selective diffusion mask pattern 36 which also serves as a protective film and which is composed of SiN. The Zn-selective diffusion mask pattern is left as it is, together with a SiON film pattern 43, which serves as a protective film, provided thereon. The structures of the light receiving element array and each light receiving element will be described in detail below with reference to FIGS. 9 and 10.

In FIG. 9, the light receiving elements 10 of the light receiving element array 50 are arranged on the common n-type InP substrate 51 (1). Current signals generated by receiving light of an SWIR band in each of the light receiving elements 10 are sent to the multiplexer 71, which also functions as a mounting substrate, and are subjected to an image-forming process, as described above. The number of pixels is changed by changing the size and pitch of the light receiving elements 10 and the size of the array. The light receiving element array 50 illustrated in FIG. 9 has 90,000 pixels. The light receiving element 10 illustrated in FIG. 10 includes a plurality of epitaxial films formed on the InP substrate 1 and also includes the selective diffusion mask pattern 36, which has been used to form the p-type region 6, for the introduction of the p-type impurity. The p-type region 6 is connected to the p-side electrode 11. The p-side electrode 11 is connected to, for example, wiring of a mounting substrate, such as the multiplexer 71, through a solder bump or the like.

Figure 11:
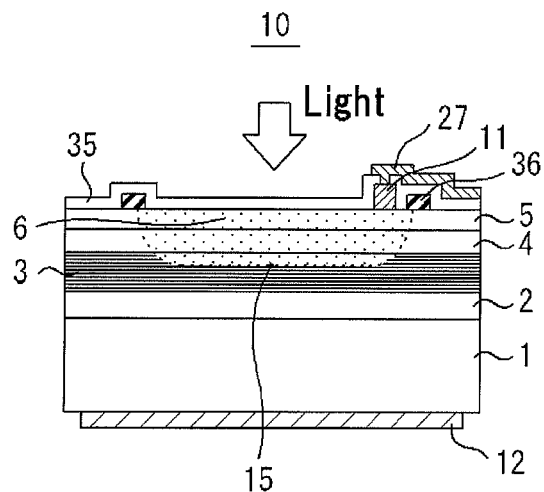
[FIG. 11]

FIG. 11 is a cross-sectional view illustrating the epi-side-up mounted light receiving element 10 different from the epi-side down mounted light receiving element 10 illustrated in FIG. 8. In the present invention, the light receiving element in the imaging device may be epi-side-down mounted or epi-side-up mounted. The light receiving element 10 includes the n-type InP buffer layer 2, the absorption layer 3, the diffusion concentration distribution control layer 4, the InP window layer 5, the selective diffusion mask pattern 36, and the antireflection (AR) film 35 provided on the n-type InP substrate 1, in that order, from the bottom. The p-type region 6 is formed so as to extend the InP window layer 5 to the pn junction 15 in the absorption layer 3 through the diffusion concentration distribution control layer 4. The n-side electrode 12 is disposed on the back surface of the n-type InP substrate 1. The p-side electrode 11 is disposed on the surface of the InP window layer 5 located in the p-type region 6 and is electrically connected to a wiring electrode 27. In this embodiment, the absorption layer 3 receives light having a wavelength of 1.0 μm to 3.0 μm. Specifically, the absorption layer 3 has the foregoing type-II multiquantum well structure.

Figure 12:
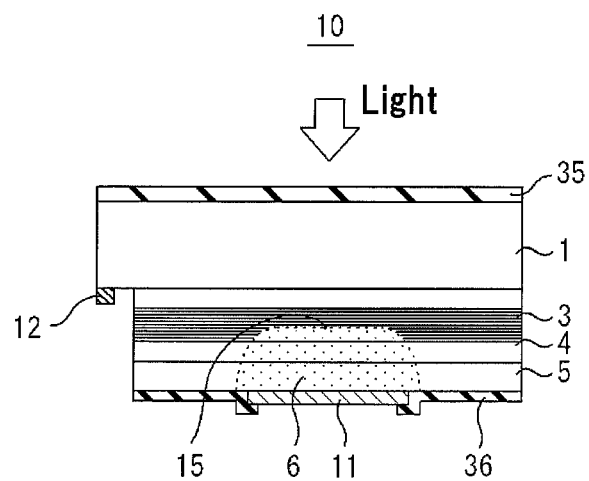
[FIG. 12]

The light receiving element 10 illustrated in FIG. 11 is epi-side-up mounted as described above. Light is incident on the epitaxial layer side, i.e., the InP window layer 5 side. The light receiving element according to this embodiment may be epi-side-up mounted or epi-side-down mounted as describe above. As illustrated in FIG. 12, the light receiving element may be epi-side-down mounted, and light may be incident on the back surface side of the InP substrate 1. For the epi-side-down mounted light receiving element 10 illustrated in FIG. 12, the AR film 35 is disposed on the back surface of the InP substrate 1. The diffusion concentration distribution control layer 4, the InP window layer 5, the p-side electrode 11, and the selective diffusion mask pattern 36, which also serves as a protective film, composed of SiN are disposed in the same way as the case of the epi-side up mounting. In the epi-side-down mounting illustrated in FIG. 12, InP constituting the InP substrate 1 and the like is transparent to light in the SWIR band; hence, light in the SWIR band arrives at the pn junction 15 in the absorption layer 3 without being absorbed. Also in the case of the structure illustrated in FIG. 12, the absorption layer 3 has the foregoing type-II multiquantum well structure. This also applies to embodiments of the present invention described below unless otherwise specified.

The p-side electrode 11 and the n-side electrode 12 may be disposed at opposite sides of the InP substrate 1 as illustrated in FIG. 11 or may be disposed on a same side of the InP substrate 1 as illustrated in FIG. 12. In the case of the structure illustrated in FIG. 12, each of the light receiving elements 10 of the light receiving element array 50 illustrated in FIG. 9 is electrically connected to an integrated circuit by flip-chip mounting. For the light receiving elements 10 having the structures illustrated in FIGS. 11 and 12, light incident on the pn junction 15 is absorbed to generate current signals. Each of the current signals is converted by the integrated circuit into a pixel image, as described above.

The InP substrate 1 is preferably an off-angle substrate that is tilted at an angle of 5° to 20° from the (100) in the [111] or [11-1] direction. More preferably, the substrate is tilted at an angle of 10° to 15° from the (100) in the [111] or [11-1] direction. The use of such a substrate having a large off-angle results in the n-type InP buffer layer 2, the absorption layer 3 having a type-II quantum well structure, the InGaAs diffusion concentration distribution control layer 4, and the InP window layer 5, each of these layers having a low defect density and good crystal quality, thereby producing the absorption layer with a suppressed dark current and only a small number of dark dots. It is thus possible to produce an absorption layer capable of markedly improving the performance of a device that receives faint cosmic light in the SWIR band to form an image. That is, the effect of the light receiving element formed using the off-angle substrate is particularly useful for improving the quality of an imaging device that receives cosmic light to form an image.

There is no proposal for the use of the InP substrate having such a large off-angle to date. The inventors have first reported that the large off-angle of the InP substrate is an important factor in growing an epitaxial film having satisfactory crystal quality on the InP substrate. Let us consider the case where, for example, a N-containing compound semiconductor, such as GaInNAs, is contained in the absorption layer 3 having the foregoing quantum well structure that is supposed to be able to emit or receive light having a very long wavelength. In this case, in fact, the absorption layer 3 cannot be formed as a satisfactory epitaxial layer that can withstand practical use if the foregoing InP substrate having a large off-angle is not used. That is, the absorption layer composed of the N-containing compound semiconductor, such as GaIn-NAs, does not have a suppressed dark current or a reduced number of dark dots if the foregoing InP substrate having a large off-angle is not used, thus failing to form a clear image using faint cosmic light in the SWIR band. Similarly to GaInNAs described above, for GaInNAsP and GaInNAsSb, the InP substrate needs to have the foregoing large off-angle range in order to achieve satisfactory crystal quality.

Each of the light receiving elements 10 illustrated in FIGS. 11 and 12 includes the InGaAs diffusion concentration distribution control layer 4 and the InP window layer 5 that cover the absorption layer 3. The lattice constant of the absorption layer 3 is equal to the lattice constant of the InP substrate 1. It is thus possible to form the InGaAs diffusion concentration distribution control layer 4, which can reliably reduce a dark current, and the InP window layer 5, thereby suppressing a dark current and improving the reliability of the element.

(Third Embodiment: Food component examination device (1)—Device for Inspecting Composition of, for Example, Fruit and Vegetables During Growth, Shipment, and So Forth—)

Figure 13:
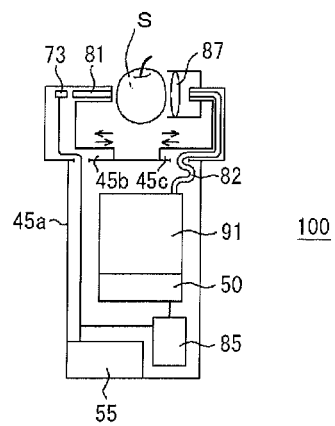
[FIG. 13]

FIG. 13 illustrates a food component examination device 100 according to a third embodiment of the present invention. A foodstuff is inspected for a composition, in particular, the sugar content, with the food component examination device 100. The light receiving element 10 or the light receiving element array 50 according to the first or second embodiment is used in such a manner that fruits, such as apples, cherries, and grapes, on trees and vegetables during growth are non-destructively inspected for the sugar content and so forth in a wide wavelength range of 1000 nm to 3000 nm with high accuracy anywhere. Furthermore, the food component examination device 100 includes a battery 55 for portable use. A light projection unit housing 45*b* and a light receiving unit housing 45*c* are movably engaged with an end portion of a main cabinet 45*a* in such a manner that the size thereof can be adjusted when a test object, such as an apple, is held. Alternatively, any one of the light projection unit housing 45*b* and the light receiving unit housing 45*c* may be movable.

Figure 14:
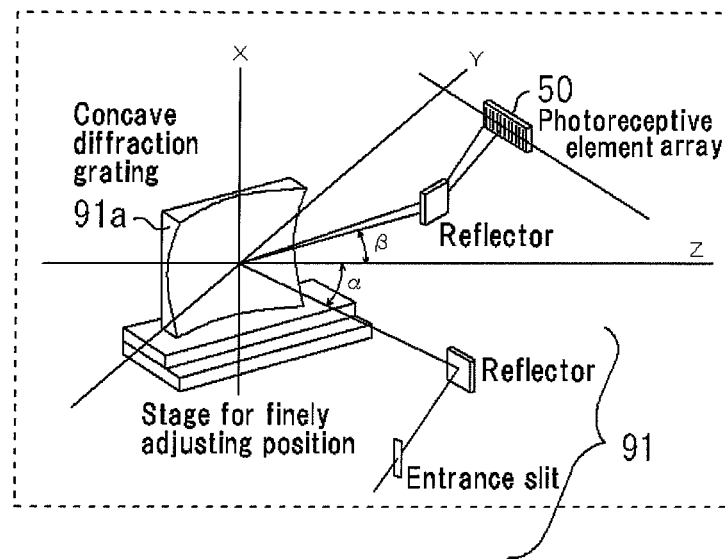
[FIG. 14]
Figure 15:
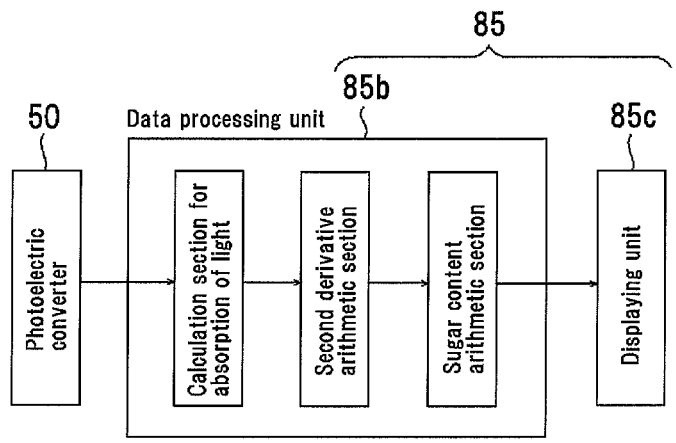
[FIG. 15]

Near infrared containing light emitted from a light source 73, such as a light-emitting diode, passes through an optical fiber 81 for light projection and emerges from a light projection and reception unit 83. A test object S, such as fruit, is irradiated with the light. Light coming through the fruit S is converged by a condenser lens 87 and guided to an entrance slit of a spectrometer unit 91 through an optical fiber 82 for light reception. FIG. 14 illustrates the spectrometer unit 91 and the light receiving element array 50. In the spectrometer unit 91, a diffraction grating 91*a*, which serves as a main member, is arranged on a stage for finely adjusting a position. Thus, angles of α and β of an optical axis with respect to a reference direction can be adjusted. The diffraction grating 91*a* diffracts the light coming through the test object S at different diffraction angles corresponding to wavelengths. The light components separated by diffraction are incident on the light receiving element array 50, i.e., a photoelectric conversion unit, and converted into electrical signals. The light receiving element array 50 may include plural light receiving elements 10. FIG. 15 illustrates a process in which the electrical signals from the light receiving element array 50 are subjected to arithmetic processing to determine the absorption of light and the sugar content. The electrical signals from the light receiving element array 50 are fed into a controller 85 and subjected to data processing using a data processing unit 85*b*, such as a microcomputer. The results are displayed on a displaying unit 85*c*.

The food component examination device 100 according to this embodiment is portably used and can measure, for example, compositions of fruit on tree and vegetables grown in soil. In particular, the food component examination device 100 is characterized in that although the device is portable, measurement is performed on the basis of light coming through the test object S. Thus, a main portion to be fed can be measured by near-infrared spectroscopy. Furthermore, in the case of the food component examination device 100, as described above, the light receiving element 10 or the light receiving element array 50 according to the first or second embodiment is used, thereby achieving a very low dark current and an electrical signal with a high S/N ratio. So, accurate detection can be achieved whether, for example, chemometrics are used or not.

For example, an exemplary method for detecting the sugar content, which is a food component, of an apple will be described. In a calculation section for the absorption of light in the data processing unit 85*b* illustrated in FIG. 15, the absorption of light having a wavelength of λ1, which is attributed to sugar, and the absorption of light having a wavelength of λ2, which is not related to sugar, are determined. Prior to the calculation of the absorption of light, it is necessary to determine calibration curves for these wavelengths. In a sugar content arithmetic section, the sugar content of a foodstuff can be calculated from the following equation using second order derivatives obtained in a second order derivative arithmetic section:

sugar content $C = K0 + K1(d2A1(\lambda1)i\ d\lambda2) + K2(d2A2(\lambda2)/d\lambda2)$, where A1(λ1) represents the absorption of light at a wavelength of λ1, A2(λ2) represents the absorption of light at a wavelength of λ2, and K0, K1, and K2 each represent a constant (coefficient) determined by, for example, the least-squares method using the absorption of light measured in a sufficiently large population and actually measured sugar contents. The absorption of light at the wavelength attributed to sugar and the wavelength unrelated to sugar is determined; hence, it is possible to detect the sugar contents of different types of test objects, such as apples, using the same calibration curve. To improve the accuracy, a third wavelength λ3, a fourth wavelength λ4, and so forth in addition to the wavelengths λ1 and λ2 may be introduced to calculate the sugar content.

(Fourth Embodiment: Food Component Examination Device (2)—Detection of Concentration Distribution of Component—)

Figure 16:
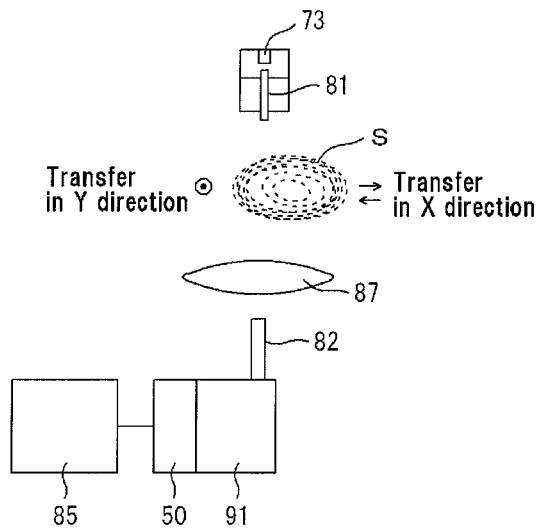
[FIG. 16]
Figure 17:
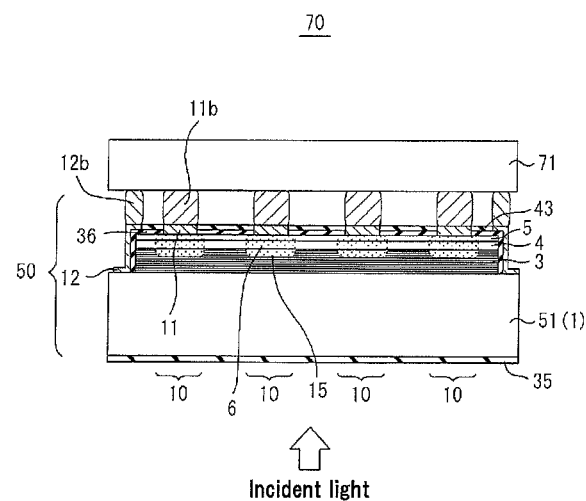
[FIG. 17]

FIGS. 16 and 17 illustrate the food component examination device 100 according to a fourth embodiment of the present invention. In this embodiment, the concentration distribution image of a component in a foodstuff is obtained, the component being contained in the foodstuff. The concentration distribution may be indices calculated from the absorption of the near-infrared light having a specific wavelength or may be function values using the foregoing absorption of light as a variable. For example, vegetables, such as leeks, Japanese radish, and carrots, and fruits, such as apples and pears, have unique features for each production area. It is difficult to visually distinguish the unique features. The near-infrared spectroscopy has the potential of distinguishing the features using concentration distributions of components in the vegetables and fruits, the components being contained in the vegetables and fruits. In particular, leeks are long in a predetermined direction. So, the production area or the brand is more likely to be identified by detecting the concentration distribution of a predetermined component, for example, sugar, along longitudinal and transverse directions. To obtain such a concentration distribution image of the component in the shape of the foodstuff, an X-Y table 46 that is movable in X-Y directions and a specimen support 47 fixed to the X-Y table are used, as illustrated in FIG. 17. Each of the X-Y table 46 and the specimen support 47 has clearance or a window so as not to interfere with near-infrared light coming through a test object S. An optical system is fixed. As illustrated in FIG. 16, one portion of the test object S is irradiated with near-infrared light, and then transmitted light is received. The transverse direction is defined as the X direction. The longitudinal direction is defined as the Y direction.

Referring to FIG. 16, light emitted from the light source 73, such as a light-emitting diode, is guided through the optical fiber 81 for light projection. A non-central portion of the test object S is irradiated with the light. Light coming through the test object S passes through the condenser lens 87, spectroscopically separated in the spectrometer unit 91, and subjected to photoelectric conversion in the light receiving unit including the light receiving element array 50 for each wavelength. Data processing and so forth on the basis of the resulting electrical signals are performed by the controller 85, thereby providing a concentration distribution image of the predetermined component. According to the detection device, it is possible to obtain a distribution in the transverse direction by transferring the X-Y table in the X direction and to obtain a distribution in the longitudinal direction by transferring the X-Y table in the Y direction. It is thus possible to conduct two-dimensional composition analysis of not only apples, pears, eggplants, cucumbers, and so forth but also long vegetables, such as leeks, Japanese radish, and carrots. This makes it possible to perform the identification of the brand and the production area and to perform the quality control by a dealer in the production area with higher accuracy. In particular, as described above, the light receiving element 10 or the light receiving element array 50 according to the first or second embodiment is used, thereby achieving a very low dark current and an electrical signal with a high S/N ratio. Thus, accurate detection can be achieved without using chemometrics and so forth or by obtaining more information using chemometrics and so forth. Enabling the identification of brand-name products allows the acquisition of the right of trademark for illicit purposes in a developing country or the like to become meaningless. To realize it, it is very appropriate to use the light receiving element 10 or the light receiving element array 50 that provides a signal having a high S/N ratio.

Figure 18:
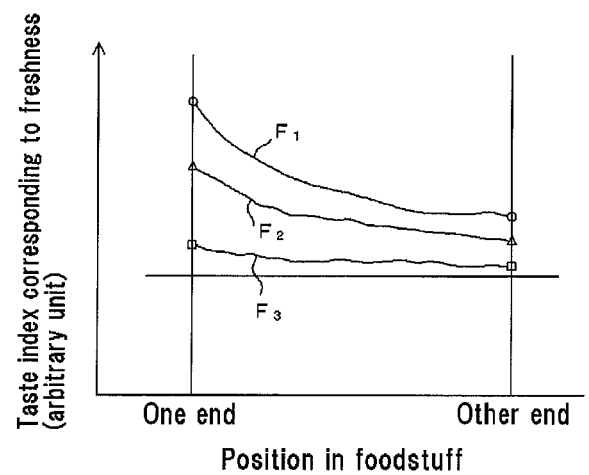
[FIG. 18]

There is a common saying, "freshly-picked vegetables are sweet". A freshness state can be inspected on the basis of this information. For example, a function in which the absorption of light corresponding to the sugar content and the absorption of light with other wavelengths are weighted is set on the basis of actual data. A value of the function is defined as a umami index corresponding to freshness. Calculation of a value of the function is automatically executable by the controller 85 if a predetermined constant is fed into the controller 85. FIG. 18 illustrates the umami index corresponding to freshness from one end to the other end of a long vegetable grown in a certain production area. A curve F1 indicates an index of that day of the harvest of the vegetable. A curve F2 indicates the index of the second day of the harvest. A curve F3 indicates the index of the third day of the harvest. In this way, the freshness state can be inspected. In particular, it is believed that a change in the freshness of a vegetable is likely to occur on the surface of the vegetable. To investigate and confirm it, as described above, the umami indexcorresponding to freshness can be determined while an irradiation position is moved in the transverse (X) direction, i.e., from the core to ends of the vegetable. In this method, the umami index corresponding to freshness is mainly set in terms of the sugar content. Alternatively, a function of a freshness index can be mainly set in terms of surface moisture and so forth, regardless of the taste.

In this case, in particular, a supercontinuum light source (SC light source) or a light-emitting diode (LED) is preferably used as the light source 73 because of a very low amount of heat generated from the light source. For example, in the case of a halogen lamp, a large amount of heat is generated, so that the freshness of a test object can be degraded.

(Fifth Embodiment: Food Component Examination Device (3)—Detection of Fat Content of Beef Carcass—)

Figure 19:
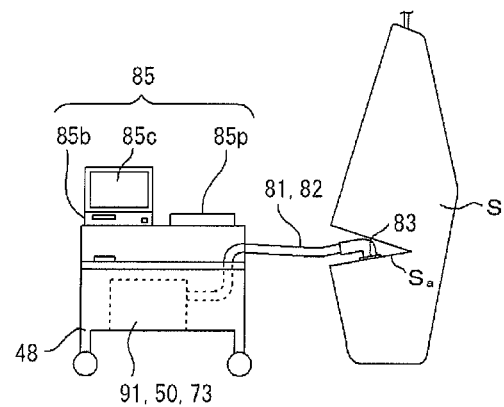
[FIG. 19]
Figure 20:
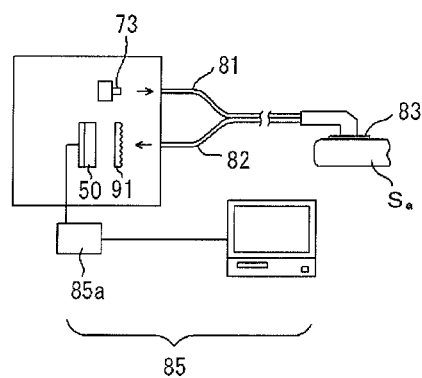
[FIG. 20]

FIGS. 19 and 20 illustrate a food component examination device according to a fifth embodiment of the present invention. In the case of the food component examination device 100 according to this embodiment, fat can be on-line detected by simply pressing the end 83 of a probe against the section Sa of a dressed carcass S without preparing a special sample, such as ground beef To realize this, the light receiving element array 50, which can reduce a dark current to obtain a signal with a high S/N ratio, described in the first and second embodiments is used in a photoelectric conversion unit.

Quality grading of beef is performed in the market of beef and the stage of circulation. With respect to this quality grading evaluation, for example, if the fat content is accurately determined by near-infrared spectroscopy in a short time, an evaluation operation by an expert can be omitted or helped. The irradiation of beef or the like with near-infrared light having a wavelength of 1000 to 2500 nm results in an absorption spectrum inherent to fat contained therein. The strong absorption attributed to a fat-specific CH group is observed at 1053 nm, 1143 nm, 1195 nm, and 1533 nm. Thus, it is known that the fat content will be detectable by measuring the absorption of light of a sample of ground meat at these wavelengths. However, for the section of a dressed carcass, the absorption of light at these wavelengths has not been obtained with sufficiently high sensitivity.

According to this embodiment, as illustrated in FIG. 20, the light receiving element array 50 described in the first and second embodiments is used in a photoelectric conversion unit. Thus, as illustrated in FIG. 19, for example, it is possible to quickly measure the absorption of light at the foregoing wavelengths with high accuracy by simply pressing the probe 83 against the section Sa of the beef carcass. In FIG. 19, the optical systems 91, 50, and 73 and the controller 85 are mounted on a rack 48 on casters. The optical systems 91, 50, and 73 are connected to the optical fiber 81 for light projection and the optical fiber 82 for light reception. As illustrated in FIG. 20, light emitted from the light source 73, such as a light-emitting diode, is passed through the optical fiber 81 for light projection. The section Sa of the beef carcass is irradiated with the light emerging from the probe 83 located at the end portion. Light reflected from the section Sa of the beef carcass is passed through the optical fiber 82 for light reception and is then incident on the diffraction grating 91, which is a main component of the spectrometer unit. The light receiving element array 50 receives light diffracted by the diffraction grating 91. The light receiving element array 50 may be replaced with the plural light receiving elements 10. Voltage signals photoelectrically converted by the light receiving elements 10 are fed into the controller 85 through an input interface 85a.

The light receiving element array 50 has a sufficiently low dark current and can output a signal having a high S/N ratio. The absorption of light can be measured with sufficiently high sensitivity at the foregoing wavelengths by simply pressing the probe 83 against the section Sa of the dressed carcass, thereby detecting the fat content of the beef. Furthermore, second order derivatives of the absorption of light at a plurality of wavelengths $\lambda 1, \lambda 2, \lambda 3$, and so forth may be calculated, and the fat content may be determined using, for example, a multiple regression expression corresponding to actual measurements of ground meat.

(Sixth Embodiment: Food Component Examination Device (4)—Detection of Abnormal Meat—)

In a sixth embodiment of the present invention, near-infrared spectroscopy is employed to detect abnormal meat. The food component examination device 100 described in the fifth embodiment is used as it is. However, the controller 85 is equipped with special software peculiar to this embodiment. PSE meat is one type of abnormal meat. The cause of generation of PSE meat remains to be fully elucidated. PSE meat refers to pale, soft, and exudative muscles after rigor and is also referred to as aged meat, steamed meat, heated meat, and so forth. Normal meat is slightly acidic. In contrast, PSE meat is strongly acidic and has a poor binding property and a low water-holding capacity. Heated PSE meat tastes bad and dry and thus is not suitable for processing. PSE meat is caused by many genetic and environmental factors, such as variety difference, strain difference in the same race, and the effect of stress before slaughter. The incidence of PSE meat tends to increase. A method for suppressing the occurrence of PSE meat has not been established yet.

For example, PTL 8 discloses that at 1109 nm in the wavelength range of 800 to 2500 nm, PSE meat has an absorption of light of about 1.1, and normal meat has an absorption of light of about 1.5, so that it is possible to distinguish them from each other. In this embodiment, the foregoing light receiving element array 50 is used. So, near-infrared light having a wavelength of 1000 nm to 3000 nm can be received and converted into a signal with a high S/N ratio. It is thus possible to measure the absorption of light having a wavelength of 1000 nm to 3000 nm with high accuracy. Furthermore, it is easily to obtain a second order derivative of the signal in the controller 85. For example, it is possible to obtain values of the absorption of light and their second order derivatives at two or more wavelengths with high accuracy. As a result, it is possible to perform the inspection of PSE meat with higher accuracy.

(Seventh Embodiment: Foreign Matter Component Examination Device—Detection of PCB and so Forth in Fat—)

Figure 21:
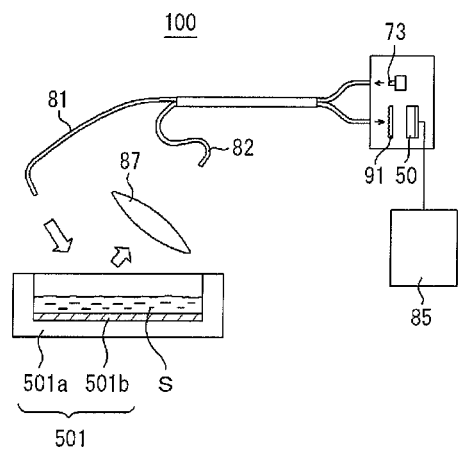
[FIG. 21]

FIG. 21 illustrates an device for detecting PCB and so forth in fat according to a seventh embodiment of the present invention. In the case of a foreign matter component examination device 100, fat is formed into a liquid by heating or with, for example, an organic solvent or enzyme. Then a halogenated organic compound, in particular, polychlorinated biphenyl (PCB), in fat is detected. The foreign matter component examination device 100 also includes the foregoing light receiving element array 50. The amount of PCB in fat is very small. So, a signal acquired is weak. It is thus very important to use the light receiving element array 50 capable of obtaining a signal with a high S/N ratio. Liquid fat S containing PCB is irradiated with near-infrared light, and reflected light is received. Thus, a reflective plating layer 501a is preferably formed on the bottom of a vessel 501. In the case where fat is formed into a liquid by heat, the vessel 501 containing the sample S is preferably equipped with a heater 501b that can assure precise temperature control. Light with which the liquid fat S containing PCB is irradiated comes through the fat S, is reflected from the reflective plating layer 501a at the bottom, comes through the fat S again, passes through the condenser lens 87, and is guided to the optical fiber 82 for light reception. The subsequent propagation of light is the same as that described above. In the case where the heater 501b is operated to thermally liquefy fat, first and second order derivatives are preferably used in order to eliminate the effect of near-infrared radiation due to thermal emission. Furthermore, measurement data in the blank state, in which a fat to be inspected is not charged thereinto, is preferably obtained. Preferably, the measurement data in the blank state is subtracted from actual data measured when the fat S is charged, thereby determining a net near-infrared spectrum of the test object S.

The use of the foreign matter component examination device 100 provides an absorption spectrum in the wavelength range of 1000 nm to 3000 nm with high accuracy. With respect to fat in which the PCB concentration has already been found, the absorption of light at a specific wavelength and the first or second order derivative of the absorption of light are correlated to produce a correlation function. Then the absorption of light and the first and second order derivatives of the fat to be inspected are determined at the specific wavelength. The concentration of PCB can be determined according to the correlation function. In the case of the foreign matter component examination device 100 according to this embodiment, the foregoing light receiving element array 50 is used, thereby achieving signals with high S/N ratios over the entire wavelength range. It is thus possible to detect PCB with high accuracy.

(Eighth Embodiment: Changed State Examination Device—Inspection of Thermal History of Food—)

A changed state examination device according to an eighth embodiment of the present invention may be the light transmission-type inspection device illustrated in FIG. 13 or 16, or may be the light reflection-type inspection device illustrated in FIG. 20. In this embodiment, for example, the thermal history of processed food of eggs is inspected. Furthermore, the device may be used for the heat control of dairy products, coffee, and cocoa. The thermal history can be used as the evaluation of sterilization treatment in combination with the production history of the food and can also be interpreted as a sterilization state.

In the case of the inspection of the thermal history according to this embodiment, it is important to carefully prepare a calibration curve (calibration spectrum) with a known thermal history. For example, the known thermal history is formed into an index of the thermal history. An important preparatory work is to find the correlation among the index of the thermal history, the absorption of light at a specific wavelength in the spectrum of the known sample, the first and second order derivatives thereof. The specific wavelength used here preferably contains a wavelength in an absorption spectrum band attributed to a component contained in eggs. Furthermore, a wavelength unrelated to egg components may be contained. The absorption of light of eggs to be inspected and the first and second order derivatives thereof are measured at the specific wavelength. An index of the thermal history can be calculated according to a correlation function produced from the preparatory work described above. The index of the thermal history is used as an evaluation value of the thermal history. Thereby, the egg product can be inspected for the thermal history.

In the case of the thermal history as described above, it is easily predicted that a change in absorption spectrum is very small, depending on foodstuffs. In this case, the use of a light receiving element having a large dark current causes difficulty in reliably performing high-accuracy inspection. According to this embodiment of the present invention, the use of the foregoing light receiving element array 50 or the light receiving element 10 enables many foodstuffs to be inspected for quality conditions. As an device similar to that according to this embodiment, there is an device for inspecting food for a freshness state, which is one of the quality conditions. Such an device has been described as the food component examination device according to the fourth embodiment (see FIG. 18). The food component examination device and so forth and the changed state examination device are not strictly distinguished. There are many fields of food inspection that can be conducted with both inspection devices.

(Ninth Embodiment: Taste Examination Device—Taste Analysis of Rice—)

Figure 22:
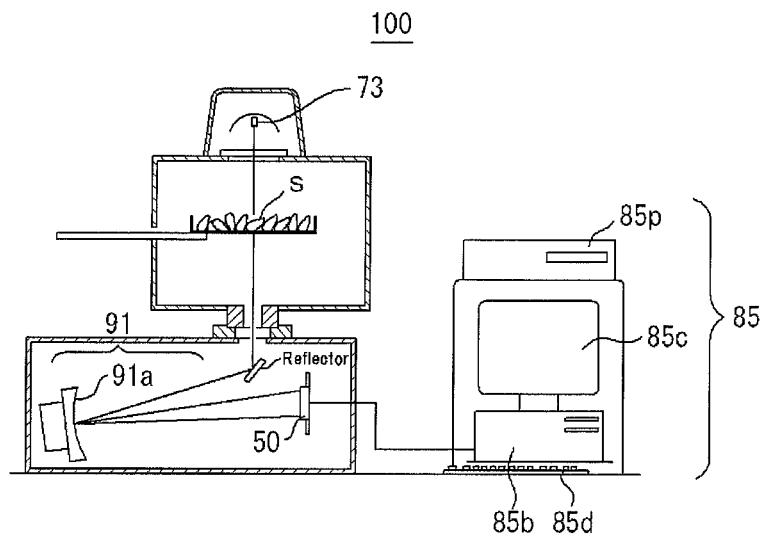
[FIG. 22]

FIG. 22 illustrates a taste examination device according to a ninth embodiment of the present invention. The taste examination device 100 is basically the same as the devices illustrated in FIGS. 13 and 16. However, the content of the controller 85 including an input unit 85d and a printer 85p is different. The term "content of the controller 85" indicates software that specifies what type of strategy is used to analyze the taste from near-infrared spectroscopic data. In FIG. 22, rice S to be analyzed may be in the form of grains or may be ground to form a powder. Near-infrared light emitted from the light source 73 comes through the rice S, is spectroscopically separated by diffraction with the diffraction grating 91, is incident on the light receiving element array 50, and is converted into electrical signals of an absorption spectrum. In this embodiment, the foregoing light receiving element array 50 or light receiving element 10 is used, thereby achieving signals with high S/N ratios up to a wavelength of 3000 nm.

In general, the quality, such as taste, depending on the senses of human beings, is determined by the contribution of not a single component but a plurality of components. For this reason, the absorption spectrum of the foodstuff in the near-infrared region is measured. Separately, the foodstuff is subjected to a sensory test by panelists to determine the sensory evaluation value of the foodstuff. The sensory evaluation value, the absorption of light at a specific wavelength in the absorption spectrum of the foodstuff, and the first or second order derivative thereof are correlated to produce a correlation function. A sensory evaluation value is determined from the near-infrared absorption spectrum of a test object on the basis of the correlation function to evaluate the taste. Which wavelength of the absorption spectrum is used in the correlation function depends on the following factors:

(1) the type of food; and
(2) the light detection range, in particular, the range where the S/N ratio is high, of the taste examination device.

Items (1) and (2) indicate that which wavelength of an absorption spectrum is used is determined, depending on not only food but also the light detection range of the taste examination device 100. Regarding a taste analysis, the following approaches can be made.

Figure 23:
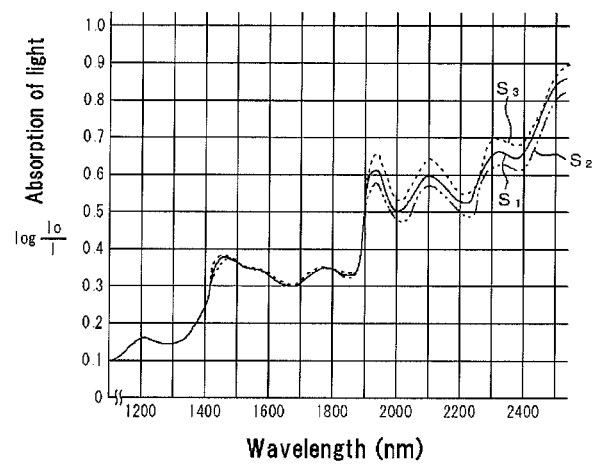
[FIG. 23]

(A1) FIG. 23 illustrates absorption spectra of three different brands S1, S2, and S3 of rice in the wavelength range of 1200 nm to 2500 nm. Components, such as amylose, protein, and water, constituting rice each have a high absorption of light at a wavelength of 1900 nm or more. It is possible to determine the absorption of light of each component. The results of the analysis of the correlation between the evaluation of the taste using the sensory test and the concentration of each component demonstrate that the taste of rice (evaluation using the sensory test) is mainly determined by the following factors: protein, amylose, and water in rice. Proportions of protein, amylose, and water are determined from the absorption of light at 2100 nm, 2130 nm, 2270 nm, and 2370 nm. It is thus possible to determine the proportions of protein, amylose, and water from the absorption of light at these wavelengths and to determine a taste value on the basis of a correlation function. That is, a taste index is expressed as $f1(x1) \cdot f2(x2) \cdot f3(x3)$, where $x1$ represents the concentration of amylose, $x2$ represents the concentration of protein, $x3$ represents the concentration of water, and $f1$, $f2$, and $f3$ each represent a function. In this approach, the taste of rice is linked to the components of rice, and then the taste is checked on the basis of near-infrared spectroscopic data.

Figure 24:
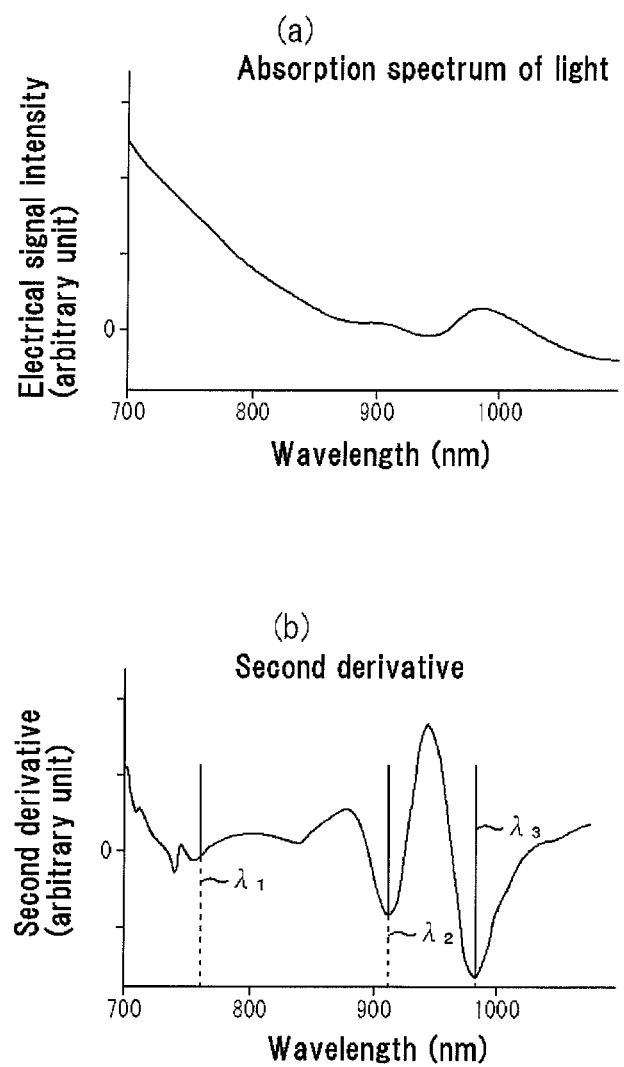
[FIG. 24] FIG. 24($a$) is an absorption spectrum of rice at short wavelengths in the near-infrared region, and FIG. 24($b$) illustrates the second order derivative of the absorption spectrum.

(A2) In this approach, the absorption of light at a specific wavelength in a relatively short wavelength range of the absorption spectrum is used as a variable of a correlation function without a correlation with the components. FIG. 24(a) is an absorption spectrum of a brand of rice. FIG. 24(b) illustrates the second order derivative of the absorption spectrum. The wavelength range is 1000 nm or less.

The light receiving element array preferably has a structure in which the InP substrate 1 is detached from the structure illustrated in FIG. 12. The InP substrate absorbs light having a wavelength of 1000 nm or less. Thus, the detachment of the InP substrate 1 enables the absorption layer 3 to receive and detect light having a wavelength of 1000 nm or less. The food quality examination device according to the present invention usually includes the InP substrate and is used. Alternatively, in particular, the InP substrate may be removed as described in the foregoing embodiment. The laminate (excluding the InP substrate) including the absorption layer is formed using the InP substrate. However, the laminate is a structural feature inherent in the device according to the present invention. Thus, the InP substrate may not be provided as described above. The laminate according to the present invention cannot be formed without using the InP substrate. So, there is no problem in specifying the food quality examination device according to the foregoing embodiment.

The second order derivative of the absorption of light at, for example, $\lambda 1$ or $\lambda 2$, in the foregoing wavelength range is correlated with the evaluation value obtained from the sensory test to produce a correlation function without a correlation with the components in rice. In this method, although the absorption of light attributed to the components, such as amylose, protein, and water, is not sharp at a wavelength of 1000 nm or less, it is speculated that the second order derivative compensates for it. Aside from the appropriateness of the speculation, the approach that correlates only the near-infrared absorption spectrum with the evaluation value obtained from the sensory test, regardless of the components, will be effective for the case of, for example, wheat-flour noodles, whose taste is affected by not only flour components but also how to make the noodles.

According to items (A1) and (A2), the taste analysis of rice can be performed with satisfactory accuracy on the basis of the near-infrared spectrum. A wavelength range used may be appropriately selected depending on, for example, a photoelectric converter of the analyzer. With respect to rice, the future challenge is to enable the brand of rice to be identified by obtaining much information using a statistical method in the widest possible wavelength range. Enabling the identification of the brand of rice allows the acquisition of the right of trademark for illicit purposes to become meaningless. To realize it, it is very appropriate to use the light receiving element 10 or the light receiving element array 50 that provides a signal having a high S/N ratio.

EXAMPLES

-Examples Regarding Structure of Semiconductor Light Receiving Element Array-

Figure 25:
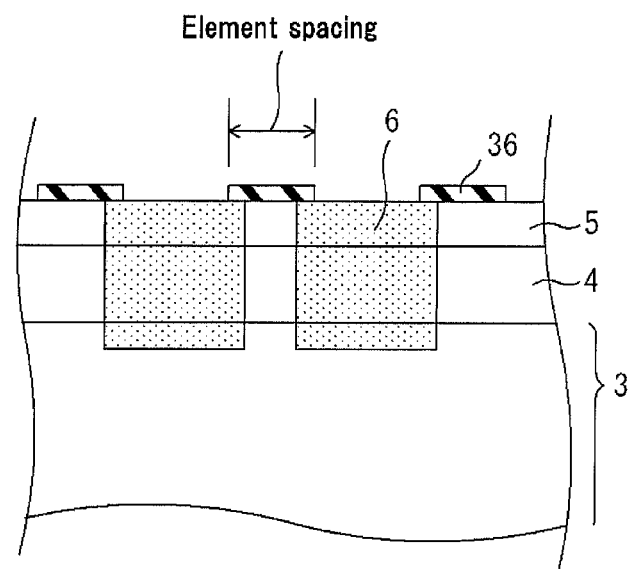
[FIG. 25]

The minimum element spacing or pixel pitch of a light receiving element array according to the present invention was examined by an example using a light receiving element array illustrated in FIG. 25. The element spacing or pixel pitch is defined as the width of a non-opening portion of the selective diffusion mask pattern 36 as illustrated in FIG. 25. After selective diffusion of Zn, the p-side electrode 11 composed of AuZn and the n-side electrode 12 composed of AuGeNi were formed. Referring to FIG. 3, an Fe-doped semi-insulating substrate is used as the InP substrate 1. So, the n-side electrode 12 is disposed on the buffer layer 2 having a high impurity content. However, in the case where the n-type InP substrate 1 is used as illustrated in FIG. 1, the n-side electrode 12 may be disposed on the back surface of the substrate. Alternatively, the n-side electrode may be disposed on an n-type semiconductor layer (for example, the buffer layer 2) adjacent to the front surface of the substrate. In this example, a reverse bias voltage of 5 V was applied between the p-side electrode 11 and the n-side electrode 12 of the light receiving element array 50 illustrated in FIG. 3 to measure a dark current. Light Receiving element arrays were produced so as to have two different thicknesses of the InP window layers 5, i.e., 0.6 μm and 1.6 μm, and seven different element spacing values in the range of 3 μm to 20 μm, and then a dark current was measured for each array. The diffusion concentration distribution control layer 4 had a thickness of 1 μm.

Figure 26:
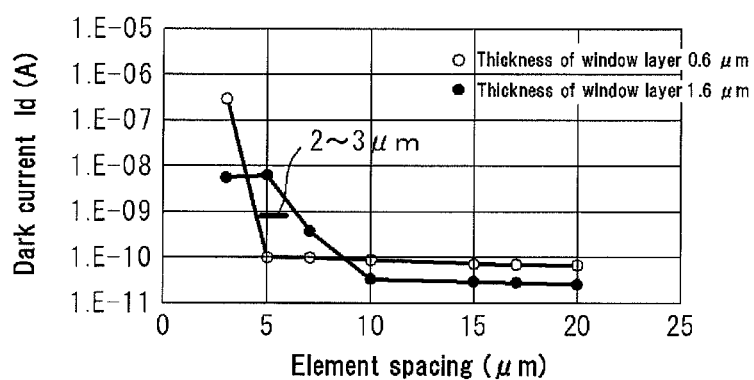
[FIG. 26]

FIG. 26 illustrates the results. Referring to FIG. 26, in the case of the InP window layer 5 having a thickness as small as 0.6 μm, even if the element spacing or the pixel pitch is reduced to 5 μm, the dark current is $1 \times 10^{-10}$ A (amperes). In the case of the InP window layer 5 having a thickness of 1.6 μm, the diffusion of Zn extends in the transverse direction as described above. It is thus impossible to obtain a dark current of $1 \times 10^{-10}$ A at an element spacing of 7 μm or less. However, this example demonstrated that an element spacing of 5 μm is obtained when the InP window layer 5 has a thickness as small as 0.6 μm and the diffusion concentration distribution control layer 4 is disposed.

Figure 27:
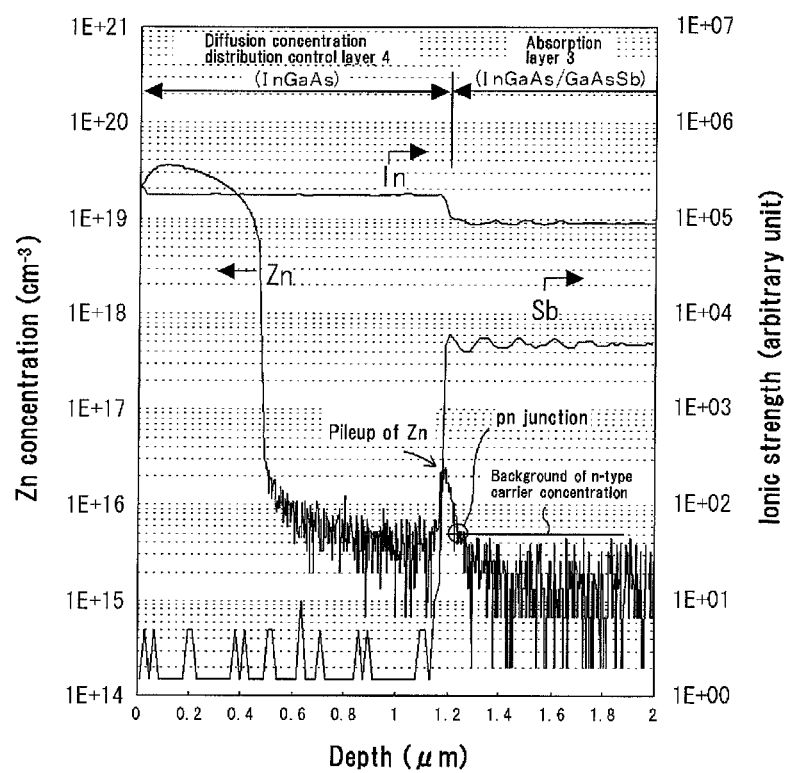
[FIG. 27]

The effect of the diffusion concentration distribution control layer 4 was verified by analyzing the distribution of Zn concentration in the depth direction using secondary ion mass spectroscopy (SIMS). FIG. 27 illustrates the distribution of Zn concentration in the depth direction. As illustrated in FIG. 27, the peak value of pileup of Zn is suppressed to $5 \times 10^{16}$ cm$^{-3}$ or less at the interface between the InGaAs diffusion concentration distribution control layer 4 and the absorption layer 3. It is thus possible to reliably reduce the Zn concentration in the pn junction formed at the intersection point (an open circle in the figure) of the background of the n-type carrier concentration of the absorption layer 3 and the Zn concentration, thereby preventing the reduction in crystal quality and so forth. The placement of the diffusion concentration distribution control layer 4 allows the multiquantum well structure of the absorption layer 3 to provide the inherent function thereof.

The embodiments and the examples of the present invention are described above. However, the embodiments and the examples of the present invention disclosed above are only illustrative, and the scope of the present invention is not limited to the specific embodiments of the invention. It is to be understood that the scope of the present invention is defined in the appended claims and includes equivalence of the description of the claims and all changes within the scope of the claims.

Industrial Applicability

According to the present invention, an innovative improvement in the performance of the InP-based PD enables highly accurate inspection as compared with the existing food quality examination devices, thereby contributing to the reliability of food. Furthermore, the present invention has the potential to bring about a change to enable brand-name food products to be identified.

What is claimed is:

1. A food quality examination device configured to inspect the quality of food comprising a light receiving element composed of III-V group semiconductor or an array of the light receiving elements, the light receiving element being configured to receive near-infrared light,
   wherein the light receiving element includes an absorption layer with a multiquantum well structure formed on an InP substrate,
   the absorption layer has a bandgap wavelength of 1.8 μm to 3 μm,
   a diffusion concentration distribution control layer composed of III-V group semiconductor and having a first surface and a second surface on opposite sides of the diffusion concentration distribution control layer, wherein the first surface is in contact with the absorption layer on a side of the absorption layer opposite the side adjacent to the InP substrate,
   the bandgap energy of the diffusion concentration distribution control layer is lower than that of the InP substrate,
   the concentration of impurity element selectively diffused in the diffusion concentration distribution control layer decreases in a direction from the second surface toward the first surface such that the concentration of the impurity element is $5 \times 10^{16}$/cm$^3$ or less at an interface between the diffusion concentration distribution control layer and the absorption layer; and
   the light receiving element receives light coming through or reflected from the food, the light having at least one wavelength of 3 μm or less, thereby performing the inspection.

2. The food quality examination device according to claim 1, wherein the concentration of the impurity element in the region located adjacent to a surface of the diffusion concentration distribution control layer opposite the surface in contact with the absorption layer being $1 \times 10^{18}$/cm$^3$ or more.

3. The food quality examination device according to Claim 1, wherein the absorption layer has a type-II quantum well structure.

4. The food quality examination device according to claim 3, wherein the absorption layer has a multiquantum well structure of (InGaAs/GaAsSb) or a multiquantum well structure of (GaInNAs(P, Sb)/GaAsSb).

5. The food quality examination device according to claim 1, wherein the InP substrate is an off-angle substrate that is tilted at an angle of 5° to 20° from the (100) in the [111] direction or in the [11-1] direction.

6. The food quality examination device according to claim 1, wherein the impurity element is zinc (Zn), and the diffusion concentration distribution control layer is composed of InGaAs.

7. The food quality examination device according to claim 1, wherein an InP window layer is disposed on the diffusion concentration distribution control layer.

8. The food quality examination device according to claim 7, wherein the degree of lattice matching, represented as |Δa/a| is 0.002 or less, wherein a represents a lattice constant, and Δa represents a difference in lattice constant among the InP substrate, sublayers constituting the quantum well structure of the absorption layer, the diffusion a concentration distribution control layer, and the RIP window layer.

9. The food quality examination device according to claim 1, further comprising a spectrometer unit arranged at the front or back of the food that is a test object. the spectrometer unit being configured to separate light, and a controller configured to perform an arithmetic operation on the basis of the result of the reception of light by the light receiving elements or the array of the light receiving elements to calculate an evaluation value of the quality of the food, wherein the plural light receiving elements or the array of the light receiving elements is located in response to the wavelength of the separated light.

10. The food quality examination device according to claim 1, wherein the food that is a test object is irradiated with light emitted from a supercontinuum light source (SC light source) or a light-emitting diode (LED), and light coming through or reflected from the food that is the test object is received.

11. The food quality examination device according to Claim I, further comprising an imaging device including a two-dimensional array of the light receiving elements, the imaging device forming a distribution image of a substance contained in the food that is a test object.

12. The food quality examination device according to claim 1, wherein in a structure in which the InP substrate is located on an incident light side, the InP substrate is removed.

13. A food component examination device comprising the food quality examination device according to claim 1, wherein the food component examination device detects a component contained in the food.

14. The food component examination device according to claim 13, wherein the concentration distribution or the like of the component contained in the food is detected in a specific range to identify the production area, the place of origin, the brand, and so forth of the food.

15. A foreign matter component examination device comprising the food quality examination device according to Claim 1, wherein the foreign matter component examination device detects foreign matter.

16. A taste examination device comprising the food quality examination device according to claim 1, wherein the taste examination device inspects rice for umami index corresponding to freshness.

17. A changed state examination device comprising the food quality examination device according to claim 1, wherein the changed state examination device inspects the food for freshness state by measuring sugar content or surface moisture.

18. The food quality examination device according to Claim I wherein a pile-up of selectively diffused impurity element is present at a boundary between the diffusion concentration distribution control layer and the absorption layer.

\* \* \* \* \*

UNITED STATES PATENT AND TRADEMARK OFFICE
CERTIFICATE OF CORRECTION

PATENT NO.       : 8,546,758 B2                                    Page 1 of 1
APPLICATION NO.  : 13/119619
DATED            : October 1, 2013
INVENTOR(S)      : Youichi Nagai et al.

It is certified that error appears in the above-identified patent and that said Letters Patent is hereby corrected as shown below:

In the Claims

Column 26, line 64, claim 8, delete "a".

Column 26, line 65, claim 8, delete "RIP" and insert -- InP --.

Signed and Sealed this
Eleventh Day of March, 2014

Michelle K. Lee
*Deputy Director of the United States Patent and Trademark Office*